US007604940B1

(12) United States Patent
Voss

(10) Patent No.: US 7,604,940 B1
(45) Date of Patent: Oct. 20, 2009

(54) COMPOSITIONS AND METHODS FOR ANALYZING ISOLATED POLYNUCLEOTIDES

(75) Inventor: Karl Voss, Foster City, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 11/375,824

(22) Filed: Mar. 15, 2006

Related U.S. Application Data

(60) Provisional application No. 60/663,001, filed on Mar. 16, 2005.

(51) Int. Cl.
C12Q 1/68 (2006.01)
C07H 21/02 (2006.01)
C07H 21/04 (2006.01)

(52) U.S. Cl. .......................... 435/6; 536/23.1; 536/24.3

(58) Field of Classification Search .................. 435/6, 435/91.2; 536/23.1, 24.3
See application file for complete search history.

(56) References Cited

U.S. PATENT DOCUMENTS

| 5,324,401 | A | * | 6/1994 | Yeung et al. | 204/452 |
|---|---|---|---|---|---|
| 5,405,746 | A | | 4/1995 | Uhlen | |
| 5,492,789 | A | * | 2/1996 | Igarashi et al. | 430/138 |
| 5,616,478 | A | | 4/1997 | Chetverin | |
| 5,674,679 | A | * | 10/1997 | Fuller | 435/6 |
| 5,821,058 | A | * | 10/1998 | Smith et al. | 435/6 |
| 5,958,698 | A | | 9/1999 | Chetverin | |
| 5,998,143 | A | * | 12/1999 | Ellis et al. | 435/6 |
| 6,001,568 | A | | 12/1999 | Chetverin | |
| 6,465,692 | B1 | * | 10/2002 | Reddy et al. | 564/215 |
| 2003/0180760 | A1 | * | 9/2003 | Basch et al. | 435/6 |
| 2004/0175733 | A1 | | 9/2004 | Andersen | |
| 2004/0185484 | A1 | | 9/2004 | Costa | |
| 2005/0079510 | A1 | * | 4/2005 | Berka et al. | 435/6 |
| 2005/0130173 | A1 | | 6/2005 | Leamon | |
| 2005/0202429 | A1 | * | 9/2005 | Trau et al. | 435/6 |
| 2006/0040297 | A1 | | 2/2006 | Saraf | |
| 2006/0074186 | A1 | * | 4/2006 | Barron et al. | 524/800 |
| 2006/0269934 | A1 | * | 11/2006 | Woudenberg et al. | 435/6 |

FOREIGN PATENT DOCUMENTS

| WO | WO2003078659 | A2 | 9/2003 |
|---|---|---|---|
| WO | WO2004069849 | A2 | 8/2004 |
| WO | WO2004070005 | A2 | 8/2004 |
| WO | WO2004070007 | A2 | 8/2004 |
| WO | WO2005003375 | A2 | 1/2005 |

OTHER PUBLICATIONS

Dinsmore et al., Colloidosomes : Selectively permeable capsules composed of colloidal particles. Science 298 : 1006-1009 (Nov. 2002).*
Nyren et al., Detection of single-base changes using a bioluminometric primer extension assay. Analytical Biochemistry 244 : 367-373 (1997.).*
Oberholzer et al., Polymerase chain reaction in liposomes. Chemistry & Biology 2 : 677-682 (1995).*
Murray, Improved double-stranded DNA sequencing using the linear polymerase chain reaction, Nucleic Acid Research 17(21):8889 (Nov. 11, 1989).*
Carothers et al., Point Mutation Analysis in a Mammalian Gene: Rapid Preparation of Total RNA, PCR Amplification of cDNA, and Tag Sequencing by Novel Method. BioTechniques 7(5):494-496, and 498-499 (May 1989).*
Krishnan et al., Linear amplification DNA sequencing directly from single phage plaques and bacterial colonies. Nuceic Acids Research 19: 1153 (1991).*
Craxton. Linear amplification sequencing, a powerful method for sequencing DNA. Methods 3 (1) : 20-26 (1991).*
Luckey et al. High-speed sDNA sequencing by capillary gel electrophoresis. Methods in Enzymology 218 : 154-172 (1993).*
Brenner et al. Gene expression analysis by massively parallel signature sequencing (MPSS) on microbead arrays: Nat Biotechnol. Jun. 2000; 18(6):630-4.
Caruso. "Hollow Inorganic Capsules via Colloid-Templated Layer-by-Layer Electrostatic Assembly" Top. Curr. Chem. 227:145-168 (2003).
Dressman et al. "Transforming single DNA molecules into fluorescent magnetic particles for detection and enumeration of genetic variations" Proc Natl Acad Sci USA. Jul. 22, 2003; 100(15):8817-22. Epub Jul. 11, 2003.
Ghadessy et al. "A novel emulsion mixture for in vitro compartmentalization of transcription and translation in the rabbit reticulocyte system" Protein Eng Des Sel. Mar. 2004; 17(3):201-4. Epub Feb. 27, 2004.
Leamon et al. "A massively parallel Pico Titer Plate based platform for discrete picoliter-scale polymerase chain reactions" Electrophoresis. Nov. 2003;24(21):3769-77.
Mitra et al. "In situ localized amplification and contact replication of many individual DNA molecules" Nucleic Acids Res. Dec. 15, 1999;27(24):e34.
Mitra et al. "Fluorescent in situ sequencing on polymerase colonies" Anal Biochem. Sep. 1, 2003;320(1):55-65.
Mitra et al. "Digital genotyping and haplotyping with polymerase colonies" Proc Natl Acad Sci USA. May 13, 2003; 100(10):5926-31. Epub May 2, 2003.
Nakano et al. "Single-molecule PCR using water-in-oil emulsion" J. Biotechnol. Apr. 24, 2003; 102(2):117-24.
Sepp et al. "Microbead display by in vitro compartmentalisation: selection for binding using flow cytometry" FEBS Lett. Dec. 18, 2002;532(3):455-8.
Shendure et al. "Advanced sequencing technologies: methods and goals" Nat Rev Genet. May 2004;5(5):335-44.
Tawfik et al. "Man-made cell-like compartments for molecular evolution" Nat Biotechnol. Jul. 1998;16(7):652-6.
Vogelstein et al. "Digital PCR" Proc Natl Acad Sci U S A. Aug. 3, 1999;96(16):9236-41.

* cited by examiner

Primary Examiner—Ethan Whisenant
(74) Attorney, Agent, or Firm—Andrew K. Finn; Life Technologies Corp.

(57) ABSTRACT

Compositions and methods of use are disclosed for the analysis of polynucleotides isolated in individual reaction compartments.

22 Claims, 6 Drawing Sheets

Sanger Reactions in Encapsulated Cells

Exchange PCR Reagents for Sequencing Reagents by Diffusion Through Cell Wall

Add Smaller Pore External Shell

↓

Thermocycle

↓

↓

Transfer to Sequencer for Injection

Methods to Add Smaller Pore External Shell

1. Encapsulation in Inverse Emulsion

2. Absorbed Single Layer or Multilayer Self Assembled Coating

COMPOSITIONS AND METHODS FOR ANALYZING ISOLATED POLYNUCLEOTIDES

1. CROSS REFERENCE TO RELATED APPLICATIONS

This application claims benefit under 35 U.S.C. § 119(e) to application Ser. No. 60/663,001, filed Mar. 16, 2005, the contents of which are incorporated herein by reference.

2. BACKGROUND

Current methods for routine and large scale analysis of target polynucleotides require the preparation of tens to thousands to millions of individual target samples, which are processed and analyzed in individual reaction vessels. Therefore, labor, materials, and equipment are a significant cost of target polynucleotide analysis regardless of the methodology employed.

To increase the number of target polynucleotides that can be discretely and simultaneously analyzed in a reaction vessel, the present disclosure provides compositions and methods for making reaction mixtures having individual reaction compartments. The reaction compartments are suitable for processing and analyzing one or more target polynucleotides by various methods.

3. SUMMARY

These and other features of the present teachings are set forth herein.

This disclosure provides compositions, methods, and kits for analyzing one or more target polynucleotide sequences.

The disclosure provides methods of analyzing the contents of a microcapsule comprising analyzing in a capillary electrophoresis system one or more molecules released from a microcapsule that is inserted into a capillary of an electrophoresis system. In some embodiments, the molecules can be produced by sequencing one or more polynucleotides contained within the microcapsule. In some embodiments, one or more molecules can be produced by sequencing one or more polynucleotides contained within an aqueous compartment of an inverse emulsion and the microcapsule can be produced by encapsulating the compartment. In some embodiments, the molecules can be sequenced by the Sanger method. In some embodiments, the polynucleotides can be attached to a surface.

In some embodiments, the polynucleotides comprise amplicons produced by clonally amplifying a target polynucleotide. In some embodiments, the target polynucleotide can be clonally amplified in a second microcapsule. In some embodiments, the target polynucleotide can be clonally amplified in an aqueous compartment of an inverse emulsion.

In some embodiments, the microcapsule comprises a hydrogel or a colloidosome. In some embodiments, a microcapsule can be produced by layer-by-layer polymer deposition or by polymer precipitation.

The disclosure also provides a sequencing method comprising clonally amplifying a target polynucleotide in an aqueous compartment of an inverse emulsion and sequencing the amplification products in a microcapsule. In some embodiments, the method further comprises analyzing the sequencing products in a capillary electrophoresis system.

The disclosure also provides a sequencing method comprising clonally amplifying a target polynucleotide in an aqueous compartment of a first inverse emulsion and sequencing the amplification products in an aqueous compartment of a second inverse emulsion. In some embodiments, the method further comprises encapsulating the aqueous compartment of the second inverse emulsion to produce a microcapsule comprising the sequencing products. In some embodiments, the method further comprises analyzing the sequencing products by a capillary electrophoresis system.

The disclosure also provides a sequencing method comprising clonally amplifying a target polynucleotide in a microcapsule, and sequencing the amplification products in an aqueous compartment of an inverse emulsion. In some embodiments, the method further comprises encapsulating an aqueous compartment of the second inverse emulsion to produce a second microcapsule comprising the sequencing products. In some embodiments, the method can further comprise analyzing the sequencing products in a capillary electrophoresis system.

The disclosure also provides a method of analyzing the contents of a plurality of microcapsules comprising analyzing in a capillary electrophoresis system molecules released from microcapsules that are inserted into the capillaries of the system. In some embodiments, the molecules can be produced by sequencing polynucleotides contained within the microcapsules. In some embodiments, the molecules can be produced by sequencing polynucleotides contained within aqueous compartments of an inverse emulsion and the microcapsules can be produced by encapsulating the compartments.

The disclosure also provides a method of placing a microcapsule into a tip of a capillary electrophoresis system comprising applying a dielectric force to a microcapsule, wherein the force directs the microcapsule to a tip of a capillary electrophoresis system. The disclosure also provides a method of placing a microcapsule into a tip of a capillary electrophoresis system comprising contacting a tip of a capillary electrophoresis system with a microcapsule. The disclosure also provides a method of placing a microcapsule into a tip of a capillary electrophoresis system comprising drawing under low pressure a suspension comprising a microcapsule and a separation polymer to a tip of a capillary electrophoresis system, whereby the microcapsule is placed into the capillary tip.

The disclosure also provides a method of seating a microcapsule at a tip of a capillary electrophoresis system comprising placing a microcapsule onto a surface; and contacting the microcapsule with a tip of a capillary electrophoresis system. In some embodiments, the surface can be an affinity pad or a well.

The disclosure also provides a method of placing a plurality of microcapsules into individual tips of a capillary electrophoresis system comprising applying a dielectric force to a plurality of microcapsules, wherein the force directs the microcapsules to individual tips of a capillary electrophoresis system. The disclosure provides a method of placing a plurality of microcapsules into individual tips of a capillary electrophoresis system comprising contacting tips of a capillary electrophoresis system with a plurality of microcapsules. The disclosure also provides method of placing a plurality of microcapsules into individual tips of a capillary electrophoresis system comprising drawing under low pressure a suspension comprising a plurality of microcapsules and a separation polymer to the tips of a capillary electrophoresis system, whereby said microcapsules are placed into individual tips. The disclosure also provides a method of placing a plurality of microcapsules into individual tips of a capillary electrophoresis system comprising placing a plurality of microcapsules onto a surface with spacing substantially matching the pitch of the tips of a capillary electrophoresis system; and contacting said microcapsule with said tips.

The disclosure also provides a composition comprising a microcapsule seated or placed in the tip of a capillary electrophoresis system.

4. BRIEF DESCRIPTION OF THE FIGURES

The skilled artisan will understand that the drawings, described below, are for illustration purposes only. The drawings are not intended to limit the scope of the present teachings in any way.

5. DETAILED DESCRIPTION

Figure 1:
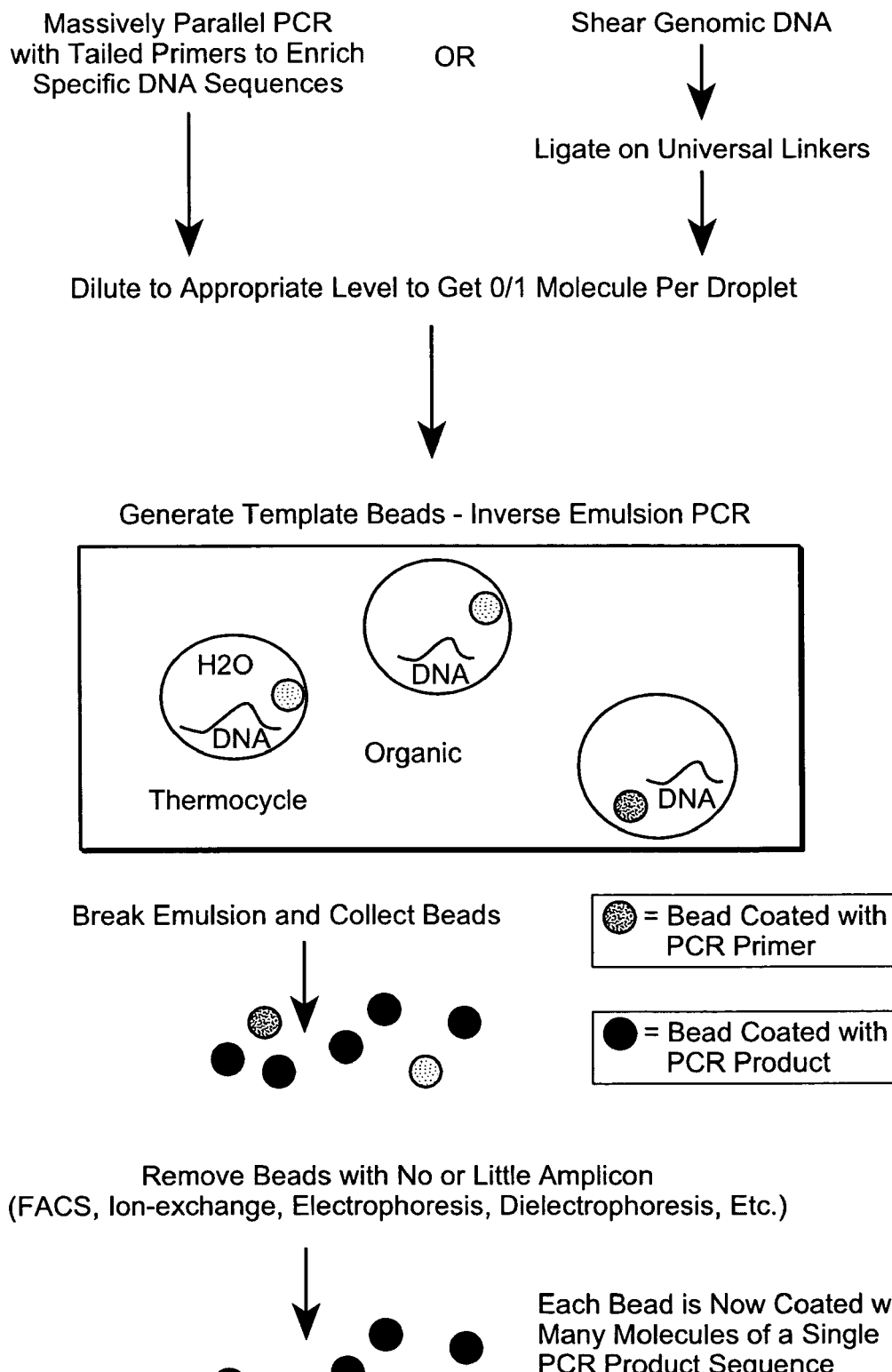
FIG. 1 illustrates embodiments of amplifying a transcriptome in a standard multiplex format and clonally amplifying the individual amplification products using a primer attached to a microparticle. In this embodiment, one strand of the double-strand amplicons attached to the microparticle can be removed from the microparticle leaving a ssDNA attached.

It is to be understood that both the foregoing general description, including the drawings, and the following detailed description are exemplary and explanatory only and are not restrictive of the disclosure. In this disclosure, the use of the singular includes the plural unless specifically stated otherwise. Also, the use of "or" means "and/or" unless stated otherwise. Similarly, "comprise," "comprises," "comprising" "include," "includes," and "including" are not intended to be limiting.

This disclosure provides compositions, methods, and kits for analyzing one or more target polynucleotide sequences. In general, the disclosure provides compositions and methods of use for analyzing one or more target polynucleotides isolated in discrete compartments of a reaction mixture. Therefore, the disclosure provides reaction mixtures comprising one or more reaction compartments. The reaction compartments form a discontinuous phase of a reaction mixture and the reaction mixture external to the reaction compartments comprise a continuous phase. As described herein, reactions suitable for the reaction compartments can be selected at the discretion of the practitioner and include, but are not limited to detection, quantitation, polymerization, amplification, sequencing, labeling, single-nucleotide polymorphism analysis, and the like.

Reaction compartments can be used in the analysis of one or more target polynucleotides in a variety of formats or modes. Such modes include but are not limited to a "single-plex" mode, in which a single target polynucleotide can be analyzed in one reaction compartment, a "multi-plex" mode, in which a plurality of target polynucleotides can be analyzed in one reaction compartment, or a "parallel" mode, in which a plurality of target polynucleotides can be analyzed in a plurality of reaction compartments. Thus, in some embodiments, a reaction mixture can comprise a plurality of reaction compartments in which a plurality of reactions can be simultaneously and discretely performed in parallel. In some embodiments, virtually any number of target polynucleotides can be simultaneously and discretely analyzed in a single reaction mixture. In contrast, standard reactions do not comprise reaction compartments and therefore the modes of such reactions include a "standard single-plex" mode, in which a single target polynucleotide can be analyzed in one reaction mixture and a "standard multi-plex" mode, in which a plurality of target polynucleotides can be analyzed in a single reaction mixture.

In various exemplary embodiments, a plurality of reaction compartments may comprise on average >0 target polynucleotides; >0 to <1 target polynucleotides, $\leq 1$ target polynucleotide, or $\leq 2$ target polynucleotides. Determining the number or average number of target polynucleotides within a reaction compartment that can be suitable for analysis is within the abilities of the skilled artisan. In addition, the skilled artisan will appreciate that the various modes can be used alone or in any combination. For example, in some embodiments, a reaction can be performed in a standard multi-plex mode and the products of can be individually utilized in a reaction performed in a parallel mode.

Thus, "reaction compartment" as used herein refers to a partitioned or discrete region or volume of a reaction mixture. As described above, one or more reaction compartments comprise a "discontinuous phase" of a reaction mixture. At least one or more or all reaction components, including intermediates, of a reaction mixture can be substantially sequestered in a reaction compartment. Exemplary embodiments of reaction components that can be substantially sequestered include but are not limited to a reactant (e.g., a target polynucleotide, a primer), a catalyst, an enzyme (e.g., a polymerase, luciferase), a cofactor (e.g., NAD, NADP, $Mg^{2+}$, $Mg^{2+}$, $Mn^{2+}$), a buffer, an intermediate, a label, and/or a product (e.g., an amplicon, an extended primer, sequencing reaction products, a ligation product, pyrophosphate), and the like. Therefore, in some embodiments, reactions substantially proceed or can be substantially confined within reaction compartments or the discontinuous phase in comparison to the continuous phase of a reaction mixture. In various exemplary embodiments, a reaction may not occur or may not proceed to completion within the continuous phase, or may proceed in the continuous but to an undetectable level, or may proceed at or above a detectable level but not to the extent that it inhibits or interferes with a reaction in the discontinuous phase and/or the analysis of the reaction products contained therein. The extent to which a reaction may occur within the various phases of a compartmentalized reaction mixture is within the abilities of the skilled artisan. Factors to be considered include but are not limited to the type of reaction, the purpose of the reaction (e.g., amplification, detection, or quantitation), or the methods of detecting the reaction products.

In some embodiments, a reaction compartment can be an aqueous compartment of an inverse emulsion. "Inverse emulsion" and "water-in-oil emulsion" ("W/O") as used herein refers to a colloidal composition comprising an aqueous liquid distributed as droplets in a hydrophobic liquid. Thus, in a reaction mixture comprising an inverse emulsion, the reaction compartments can be aqueous droplets which comprise the discontinuous phase and can be distributed in a hydrophobic continuous phase. "Microemulsion" are used herein refers to an inverse emulsion in which an aqueous droplet can have an external and/or internal diameter from 1 µm to about 500 µm, from about 1 µm to about 300 µm, from about 1 µm to about 200 µm, from about 10 µm to about 100 µm, and/or from about 25 µm to about 75 µM. In some embodiments, an aqueous droplet of a microemulsion can have a volume from about 0.5 µm$^3$ to about 4,000,000 µm$^3$, from about 500 µm$^3$ to about 500,000 µm$^3$, from about 8,000 µm$^3$ to about 200,000 µm$^3$. However, the skilled artisan will appreciate that larger and smaller droplets also can be contemplated.

The composition of the continuous and discontinuous phases of an inverse emulsion can be selected at the discretion of the practitioner. As described above, a continuous phase can be hydrophobic and therefore can include but is not limited to an oil (e.g., mineral oil, light mineral oil, silicon oil) or a hydrocarbon (e.g., hexane, heptane, octane, nonane, decane) and the like. In contrast, the discontinuous phase can be an aqueous solution that provides conditions suitable for analysis of a target polynucleotide. The composition of the various phases are selected to provide a suitable emulsion under the conditions selected for carrying out the reaction in the aqueous compartments. Therefore, "suitable emulsion" refers to an emulsion that does not substantially degrade, collapse and/or in which the aqueous droplets do not substantially coalesce under the reaction conditions. Therefore, in some embodiments, an emulsion can be suitable for carrying out reactions at various temperatures (e.g., thermocycling, such as, PCR, LCR, cycle sequencing etc.), and other various conditions (e.g., pH, ionic strength, hybridization conditions, etc.), and in the presence of various reaction components (e.g., nucleic acids, proteins, enzymes, catalysts, co-factors, intermediates, products, by-products, labels, microparticles, etc.).

In some embodiments an emulsion can comprise compositions or compounds that modify the emulsion's stability. In some embodiments, such compounds can be amphipathic and therefore comprise hydrophobic and hydrophilic groups. In various exemplary embodiments, the hydrophilic group can be polar and/or positively and/or negatively charged. That skilled artisan can appreciate that amphipathic compounds, depending on their concentration and the composition of the various phases, can be used to increase or decrease the emulsion stability. Examples of amphipathic compounds include but are not limited to proteins, polypeptides, and surfactants, such as, detergents and emulsifiers, all of which can be used alone or in any combination. For example, an amphipathic compound can be a protein or polypeptide (e.g., albumin), lecithin, sodium oleate, glycolic acid ethoxylate oleyl ether, 4-(1-aminoethyl)phenol propoxylate, glycolic acid ethoxylate 4-tert-butylphenyl ether, glycolic acid ethoxylate oleyl ether, sodium dodecyl sulfate, 3-[(3-cholamidopropyl)dimethylammonia]-1-propanesulfonate, n-dodecyl-o-D-maltoside (lauryl-β-D-maltoside), n-octyl-β-D-glucopyranoside, n-octyl-β-D-thioglucopyranoside (OTG), 4-(1,1,3,3-tetramethylbutyl)phenol polymer, N-lauroylsarcosine, polyethylene-block-poly(ethylene glycol), sodium 7-ethyl-2-methyl-4-undecyl sulfate, glycolic acid ethoxylate lauryl ether, Atlox® 4912, Tween® 20, Tween® 80, sorbitan monooleate (Span 80), Triton® X-100, Triton® X-114, Brij®-35, Brij®-58, 3-[(3-cholamidopropyl)-dimethylammonio]-1-propanesulfonate (CHAPS), Nonidet P-40 (NP-40). For further description of these and/or other amphipathic compounds and methods of use in emulsions see, e.g., Becher, *Emulsions: Theory and Practice*, 3rd ed. Oxford University Press 2001 (ISBN 0841234965); Becher (ed.) *Encyclopedia of Emulsion Technology: Basic Theory Vol. 1-IV*, Marcel Dekker Inc. 1983 (ISBN: 0824718763), 1985 (ISBN: 0824718771), 1987 (ISBN: 082471878X), 1996 (ISBN: 0824793803); Holmberg, *Surfactants and Polymers in Aqueous Solutions* 2nd ed., John Wiley & Sons 2002 (ISBN: 0471498831); Lissant (ed.), *Emulsions and Emulsion Technology*. Marcel Dekker Inc. 1984 (ISBN: 0824770838); Lissant, *Emulsions and Emulsion Technology (Surfactant Science)*. Marcel Dekker Inc. 1974 (ISBN: 0824760972); Lissant (ed.), *Emulsions and Emulsion Technology/Part II* (Surfactant Science, Vol. 6). Marcel Dekker Inc. 1974 (ISBN 0824718925); Lissant, *Emulsions and Emulsion Technology* Marcel Dekker Inc. 1984 (ISBN: 0824790472); *Handbook of Industrial Surfactants* (ISBN 1890595209).

Methods of making inverse emulsions are known in the art and include but are not limited to drop wise addition of an aqueous solution comprising a reaction mixture to a stirred hydrophobic phase optionally comprising one or more amphipathic compounds. (Becher, *Emulsions: Theory and Practice,* 3rd ed. Oxford University Press 2001 (ISBN 0841234965); Becher (ed.) *Encyclopedia of Emulsion Technology: Basic Theory Vol. 1-IV*, Marcel Dekker Inc. 1983 (ISBN: 0824718763), 1985 (ISBN: 0824718771), 1987 (ISBN: 082471878X), 1996 (ISBN: 0824793803); Dressman et al., 2003, *Proc. Natl. Acad. Sci.* USA. 100(15):8817-22 (Epub 2003 July 11); Ghadessey et al., 2001, *Proc. Natl. Acad. Sci.* USA. 98:4552-7; Griffiths et al., 2003, *EMBO* 22:24-35; Lissant (ed.), *Emulsions and Emulsion Technology*. Marcel Dekker Inc. 1984 (ISBN: 0824770838); Lissant, *Emulsions and Emulsion Technology (Surfactant Science)*. Marcel Dekker Inc. 1974 (ISBN: 0824760972); Lissant (ed.), *Emulsions and Emulsion Technology/Part II* (Surfactant Science, Vol. 6). Marcel Dekker Inc. 1974 (ISBN 0824718925); Lissant, *Emulsions and Emulsion Technology* Marcel Dekker Inc. 1984 (ISBN: 0824790472); Nakano et al., 2003, *J. Biotechnol.* 102(2):117-24; Tawfik et al., 1998, *Nat. Biotechnol.* 16(7):652-6; U.S. Pat. No. 6,489,103; and WO 2002/22869). In some embodiments, emulsion formation can be monitored by high-resolution ultrasonic spectroscopy in which changes in ultrasonic velocity and attenuation that occur as a function of time are indicative of emulsion formation, as known in the art. In some embodiments, the size (e.g., mean droplet diameter), number, and/or composition of the aqueous phase droplets can be analyzed microscopically (Dressman et al., 2003, *Proc. Natl. Acad. Sci.* USA. 100(15):8817-22 (Epub 2003 July 11) or by laser diffraction (Tawfik et al., 1998, *Nat. Biotechnol.* 16(7):652-6).

In various exemplary embodiments, the products produced in the reaction compartments of an inverse emulsion can be analyzed or can be used for further downstream reactions, which in some embodiments, can be conducted in an inverse emulsion or microcapsules or standard reactions, as described below. In some embodiments, the reaction compartments can be analyzed without demulsification ("breaking the emulsion") (e.g., microscopically, laser diffraction, laser Doppler velocimetry/anemometry ("LDV" or "LDA"), and/or fluorescence). In some embodiments, an emulsion can be broken and the contents of the reaction compartments can be collected. In some embodiments, such as reactions performed in parallel, the contents of the individual reaction compartments can be individually collected and/or identified for further use as described below. Methods of breaking an inverse emulsion are known in the art and include but are not limited to the use of detergents, organic solvents, centrifugation, and/or temperature (Dressman et al., 2003, *Proc. Natl. Acad. Sci.* USA. 100(15):8817-22 (Epub 2003 July 11; Tawfik et al., 1998, *Nat. Biotechnol.* 16(7):652-6).

In some embodiments, a reaction compartment can be a microcapsule. "Microcapsule" as used herein refers to a hollow device suitable for providing a reaction compartment of a reaction mixture. In various exemplary embodiments of reaction mixtures comprising microcapsules, the continuous phase can be aqueous or hydrophobic and the microcapsules comprise a discontinuous aqueous phase. In some embodiments, a microcapsule can be placed in an inverse emulsion. In some embodiments, the external and/or internal diameter of a microcapsule can be from about 50 µm to about 100 µm in diameter. In some embodiments, the external and/or internal volume of a microcapsule can be from about 65,000 µm$^3$ to 550,000 µm$^3$. However, the skilled artisan will appreciate that larger and smaller microcapsules also can be contemplated.

In some embodiments, the contents of a microcapsule and the continuous phase can be in fluidic communication. Therefore, in some embodiments, various molecules (e.g., reaction components) can pass between a microcapsule and the continuous phase. In some embodiments, fluidic communication can be by size selective passive transport mechanisms. For example, in some embodiments some molecules can pass through a microcapsule wall to and/or from the various reaction mixture phases (e.g., diffusion). In some embodiments, some molecules can pass through a one or more microcapsule pores. "Pore" and grammatical equivalents herein refer to an opening, hole, or perforation in the wall of a microcapsule. In some embodiments, the pores of one or more microcapsule can be substantially equivalent (i.e., ranging in surface area by ≦5%). In some embodiments, the pores of a microcapsule can be modified to alter the reaction components that are capable of entering or exiting a microcapsule at various steps of the disclosed. For example, in various embodiments a polymer solution (e.g., polyacrylamide) can be absorbed to a microcapsule or removed from a microcapsule to decrease or increase pore size, respectively. In some embodiments, a force (e.g., an electric field) can be applied to insert and/or remove reaction components from a microcapsule.

Some depicted embodiments may refer to microcapsules having a generally spherical shape; however, a microcapsule can have any shape, for example, egg-shaped, tubular, cylindrical, cubical, irregularly shaped and the like. In various exemplary embodiments, the structure of a microcapsule can be rigid, inflexible, deformable, or elastic. In some embodiments, a microcapsule can be opaque, translucent, and/or transparent. In some embodiments a signal (e.g., fluorescent, phosphorescent, chemiluminescent, magnetic signal, etc.) in a microcapsule can be induced, detected, and/or quantitated. In some embodiments, capsule can be identified, analyzed and/or sorted, e.g., by flow cytometry, microflow cytometry (see, e.g., U.S. Pat. No. 6,710,871, U.S. Application Nos. 20020028434 and 20040036870; EP1397666, WO 02/093138, WO 02/21102, WO 98/57152, WO 2004/037157), dielectrophoresis, including traveling wave dielectrophoresis (Pethig, 2003, *Electrochemistry* 71:203-205; Pethig et al., 2002, *Electrophoresis* 23:2057-2063; U.S. Pat. Nos. 5,653,859 5,795,457 5,814,200 5,993,631 6,197,176, 6,264,815; U.S. Patent Application Nos. 20030029714 and 20040112748; EP0680380, EP0815942, EP0914211, EP1092477, and WO 91/11262, WO 94/16821, WO 98/04355, and WO 2004/055505).

Selecting the appropriate features of a microcapsule for the uses described herein is within the abilities of the skilled artisan. Non-limiting exemplary parameters that can be considered in the design of a microcapsule include but are not limited to the number and type of reactions occurring within the microcapsule, the type of reactants, products, and/or intermediates, the order in which the reactions may be performed, and the detection and/or quantitation method employed.

Microcapsules can be synthesized by various methods, as known in the art. In some embodiments, microcapsules can be constructed within a reaction mixture. Therefore, in some embodiments the components of a reaction mixture can be placed and/or captured in a microcapsule during microcapsule synthesis. In some embodiments, one or more or all of the components of a reaction mixture can be introduced into a microcapsule after synthesis. In some embodiments, a reaction component can be introduced into a microcapsule through one or more pores, diffusion, and/or other methods, described above.

Methods of synthesizing microcapsules are known in the art. For example, in some embodiments a molecule to be encapsulated is mixed throughout another material to form a solid microsphere, which can be dissolved and/or exits the microsphere by, for example, passive diffusion. In some embodiments, microcapsules can be produced by synthesizing the capsule wall around various templates (e.g., latex, silica sols, living cells, inorganic spheres, surfactant vesicles, block copolymer vesicles, emulsion droplets, and gas bubbles). In various exemplary embodiments, a microcapsule wall can comprise an organic polymer, an inorganic compound, and/or a composite organic/inorganic composite (see, e.g., Meier, 2000, *Chem. Soc. Rev.* 29:295-303).

Methods of synthesizing microcapsules include but are not limited to production by polymerization and self-assembly methods (Discher et al., 1999, *Science* 284:1143; Huang et al., 1999, *J. Amer. Chem. Soc.* 121:3805; Holtz et al., 1998, *Langmuir* 14:1031; Jenekhe et al., 1998, *Science* 279:1903; Okubo et al., 1998, *Colloid Polym. Sci.* 276:638; Sanji et al., 2000, *Macromolecules* 33:8524; Wendland et al., 1999, *J. Am. Chem. Soc.* 121:1389; Zhao et al., 1998, *J. Am. Chem. Soc.* 120:4877), photochemical degradation of polysilane shell cross-linked micelles (Sanji et al., 2000, *Macromolecules* 33:8524-8526), ozonolysis of shell cross-linked micelles with poly-(isoprene)-b-poly(acrylic acid) (Huang et al., 1999, *J. Am. Chem. Soc.* 121:3805), modification of microporous polycarbonate filtration membranes (Parthasarathy et al., 1994, *Nature* 369:298-301), γ irradiation to initiate the formation of hollow CdS/polystyrene composites (Wu et al., 2004, *Langmuir* 20:5192-5195), and suspension polymerization (Okubo et al., 1998, *Colloid Polym. Sci.* 276:638-642).

In some embodiments, microcapsules can be synthesized by a layer-by-layer (LbL) electrostatic assembly process (Caruso et al., 1998, Science 282:1111; Caruso, 2000, *Chem. Eur. J.* 6:413; Caruso, 2003, *Top. Curr. Chem.* 227:145-169; Donath et al., 1998, *Angew. Chem. Int. Ed.* 37:2201; Capsulation NanoScience AG, Cologne, Germany). Generally, in this process, a compound having a first charge can be layered onto a template and/or preceding layer having the opposite charge. This process can be repeated by successively adding layers of opposite charge to the previous layer. The number and composition of layers can be selected at the discretion of the practitioner to synthesize a microcapsule have desired properties (e.g., rigidity, flexibility, elasticity, mechanical strength, porosity, permeability, thermal properties, optical properties). In some embodiments, a microcapsule does not substantially bind the components of a reaction contained therein. In some embodiments, the amount of material added for each layer can be insufficient to form a saturated layer. Therefore, in some embodiments, the amount of material utilized for each layer can be used to control the porosity of the microcapsule. In some embodiments, the template can be removed from the microcapsule by various methods, as known in the art, including but not limited to temperature (e.g., calcination) and chemical methods.

In various exemplary embodiments, a template for microcapsule synthesis can be a colloid (e.g., polymer (Caruso et al., 1998, *Science* 282:1111; Donath et al., 1998, *Angew. Chem. Int. Ed.* 37:2201), a metal particle (Gittins et al., 2000, *Adv. Mater.* 12:1947), protein crystals (Caruso et al., 2000, *Langmuir* 16:1485), low molecular weight compounds (Caruso et al., 2000, *Langmuir* 16:89323), a cell (Caruso, 2000, *Chem. Eur. J.* 6:413; Moya et al., 2000, *Macromolecules* 33:4538), melamine formaldehyde microparticle, or a polystyrene microparticle. In various exemplary embodiments, the materials used to layer the template include but are not limited to polyelectrolytes (e.g., poly(diallyldimethylammonium chloride (PDADMAC) (Donath et al., 1998, *Angew. Chem. Int. Ed.* 37:2201; Caruso et al., 1999, *Chem. Mater.* 11:3394; Caruso et al., 2000, *Langmuir* 16:1485; Caruso et al., 2000, *Langmuir* 16:89323; Gittins et al., 2000, *Adv. Mater.* 12:1947; Moya et al., 2000, *Macromolecules* 33:4538)), nanoparticles (e.g., $SiO_2$ nanoparticles (Caruso et al., 1999, *Adv. Mater.* 11:950; Caruso et al., 2001, *Chem. Mater.* 13:400; Caruso et al., 2001, *Chem. Mater.* 13:109 45; Caruso et al., 2001, *Adv. Mater.* 13:1090; Cassagneau et al., 2002, *Adv. Mater.* 14:732; Gittins et al., (2002) *Adv. Mater.* 14:508; Rhodes et al., 2000, *Chem. Mater.* 12:2832 43; Rogach et al., 2000, *Adv. Mater.* 12:333; Susha et al., 2000, *Colloids Surf. A. Physicochem. Eng. Aspects.* 163:39), and inorganic molecule precursors (e.g., titanium (IV) bis(ammonium lactano) dihydroxide (TALH: $[CH_3CH(O—)CO_2NH_4]_2 Ti(OH)_2)$).

In some embodiments, a hydrogel microcapsule can be synthesized by interfacial polymerization in an inverse emulsion (Arshady, 1989, *J. Microencapsul.* 6(1):13-28; Makino et al., 1998, *Colloids and Surfaces B:Biointerfaces* 12:97-104). In some embodiments, the size of a hydrogel microcapsule can be controlled by controlling the droplet size in the inverse emulsion. Capsule wall permeability can be adjusted by changing conditions, e.g., pH. (Nagashima et al., 1998, *Colloids and Surfaces B: Biointerfaces* 11:47-56, Narita et al., 2003, *Langmuir* 19:4051-4054.)

In some embodiments, microcapsules (i.e., colloidosomes) can be produced by self-assembly of colloidal particles at the interface of an inverse emulsion. In this method, small latex particles from an acrylic latex assemble around an aqueous emulsion droplet. The latex particles can be locked together by addition of a polycation or by sintering. The space between the assembled latex particles controls the permeability of the microcapsule. Sintering can proceed by raising the temperature slightly above the glass transition temperature of the polymer in the latex. For example, in some embodiments PMMA particles can be sintered in about 5 minutes at 105° C. (Dinsmore et al., 2002, *Science* 298:1006-1009). Because the latex particles assemble at W/O surface to minimize surface energy, an effect generally independent of the latex chemistry, many polymers other than PMMA can be employed.

In some embodiments, a microcapsule (e.g., polysulfone microcapsules) can be synthesized by liquid-liquid phase separation techniques (Zhao et al., 2004, *J. Microencapsulation* 21:283-291). In this method, a polymer solution can be brought into contact with a solution in which the polymer is insoluble resulting in polymer precipitation at the interface. (see, e.g. U.S. Pat. Nos. 3,943,065, 4,353,888, 5,441,878, 5,492,789, 5,571,415, 5,691,431, 5,733,462, 5,830,960, 5,837,790, 5,885,032, 5,934,839, 5,985,354, 6,013,708, 6,046,293, 6,248,849, 6,387,995, 6,511,749, 6,528,035, 6,528,093, 6,583,251, 6,599,627, 6,623,764.).

Reaction compartments can be used in the analysis of one or more target polynucleotides. As will be appreciated by skilled artisans, target polynucleotides can comprise one or more target sequences suitable for analysis and may be either DNA (e.g., cDNA, genomic DNA, extrachromosomal DNA (e.g. mitochondrial DNA, plasmid DNA), an amplicon) or RNA (e.g., mRNA, rRNA, tRNA, an in vitro transcript, or genomic RNA (e.g., virion RNA (vRNA)) in nature, and may be derived or obtained from virtually any sample or source, wherein the sample may optionally be scarce or of a limited quantity. For example, the sample may be one or a few cells collected from a crime scene or a small amount of tissue collected via biopsy. In various exemplary embodiments, a cell can be a prokaryotic (e.g., bacterium) or eukaryotic cell (e.g., leukocyte, epithelial cell, neuronal cell, connective tissue cell, muscle cell, stem cell etc.), including but not limited to transformed, transfected, and/or infected cells. In some embodiments, the target polynucleotide may be a synthetic polynucleotide comprising nucleotide analogs or mimics, as described below, produced for purposes, such as, diagnosis, testing, or treatment.

In various non-limiting examples, the target polynucleotide may be single or double-stranded, or a combination thereof, linear or circular, a chromosome or a gene or a portion or fragment thereof, a regulatory polynucleotide, a restriction fragment from, for example, a plasmid or chromosomal DNA, genomic DNA, mitochondrial DNA, DNA from a construct or library of constructs (e.g., from a YAC, BAC or PAC library), RNA (e.g., mRNA, rRNA or vRNA) or a cDNA or a cDNA library. As known in the art, a cDNA is a single- or double-stranded DNA produced by reverse transcription of an RNA template. Therefore, some embodiments include a reverse transcriptase and one or more primers suitable for reverse transcribing an RNA template into a cDNA. Reactions, reagents and conditions for carrying out such "RT" reactions are known in the art (see, e.g., Blain et al., 1993, *J. Biol. Chem.* 5:23585-23592; Blain et al., 1995, *J. Virol.* 69:4440-4452; *PCR Essential Techniques* 61-63, 80-81, (Burke, ed., J. Wiley & Sons 1996); Gubler et al., 1983, *Gene* 25:263-269; Gubler, 1987, *Methods Enzymol.*, 152:330-335; Sellner et al., 1994, *J. Virol. Method.* 49:47-58; Okayama et al., 1982, *Mol. Cell. Biol.* 2:161-170; and U.S. Pat. Nos. 5,310,652, 5,322,770, and 6300073, these disclosures of which are incorporated herein by reference.

A target polynucleotide may include a single polynucleotide, from which one or more different target sequences of interest may be amplified, or it may include a plurality of different polynucleotides, from which one or more different target sequences of interest may be amplified. As will be recognized by skilled artisans, the sample or target polynucleotide may also include one or more polynucleotides comprising sequences that are not analyzed by the disclosed methods. Thus, in some embodiments, the sequences analyzed can be selected at the discretion of the practitioner.

In some embodiments, highly complex mixtures of target sequences from highly complex mixtures of polynucleotides are amplified in various exemplary modes, described above. For example, many embodiments can be suitable for parallel analysis of target sequences from tens, hundreds, thousands, hundreds of thousands or even millions of polynucleotides. In some embodiments, pluralities of target sequences from samples comprising cDNA libraries or total mRNA (e.g., a transcriptome) isolated or derived from biological samples, such as tissues and/or cells, wherein the cDNA or, alternatively, mRNA libraries may be quite large can be analyzed in parallel. For example, cDNA libraries or mRNA libraries constructed from several organisms or from several different types of tissues or organs can be amplified according to the methods described herein. Therefore, in some embodiments a plurality of target sequences includes, but is not limited to, a genome or transcriptome of one or more cells or tissues or organisms. For example, in some embodiments, a transcriptome can be analyzed at any one or more stages of a cell cycle, or differentiation, or response to natural or artificial stimuli.

The reactions that can be performed within the reaction compartments are selected at the discretion of the practitioner. Such reactions suitable for the analysis of a target polynucleotide include but are not limited to PCR (see, e.g., U.S. Pat. Nos. 4,683,195, 4,683,202, 4,800,159, 4,965,188, 5,075, 216, 5,176,995, 5,338,671, 5,340,728, 5,386,022, 5,333,675, 5,405,774, 5,436,149, 5,512,462, 5,618,703, 5,656,493, 6,037,129, 6,040,166, 6,197,563, 6,300,073, 6,406,891, 6,514,736; EP-A-0200362, EP-A-0201184, U.S. Ser. No. 60/584,665, Edwards et al. (eds.), 2004, Real-Time PCR: An Essential Guide. Horizon Bioscience Norfolk, UK (ISBN 0-9545232-7-X); Innis et al., 1990 In: PCR Protocols A Guide to Methods and Applications, Academic Press, San Diego), LCR (see, e.g., EP-A-320308 and U.S. Pat. Nos. 5,427,930, 5,516,663, 5,686,272, and 5,869,252), OLA (see, e.g. U.S. Pat. No. 4,883,750), Q-beta amplification (see, e.g. U.S. Pat. Nos. 4,786,600 and 4,957,858, "Amplifying Probe Assays with Q-Beta Replicase" Bio/Technology 1989: 7(6), 609-10 (Eng.); Pritchard, 1990, *J. Clin. Lab. Anal.* 4:318), NASBA™ (Burchill et al., 2002, *Br. J. Cancer.* 86(1):102-9; Deiman et al., 2002, *Mol. Biotechnol.* 20(2):163-79; Malek et al. "Nucleic Acid Sequence-Based Amplification (NASBA™)" Ch. 36 In Methods in Molecular Biology, Vol. 28: Protocols for Nucleic Acid Analysis by Nonradioactive Probes, Isaac (ed.) Humana Press, Inc., Totowa, N.J. (1994); Romano et al., 1997, *Immunol. Invest.* 26(1-2): 15-28), rolling circle amplification (see, e.g., U.S. Pat. No. 5,714,320), strand displacement amplification ((SDA) U.S. Pat. Nos. 5,270,184 and 5,455,166; Walker. "Empirical Aspects of Strand Displacement Amplification" In PCR Methods and Applications, 3(1):1-6 Cold Spring Harbor Laboratory Press, Cold Spring Harbor, N.Y. (1993), other amplification methods and techniques (see, e.g., Andras-et al., 2001, *Mol. Biotechnol.* 19(1):29-44; Frohman, 1994, *PCR Methods Appl.* 4(1):S40-58; Frohman et al., 1993, *Methods Enzymol.* 218: 340-56; Hawkins et al., 2002, *Curr. Opin. Biotechnol.* 13(1): 65-7; Kwoh et al., 1989, *Proc. Natl. Acad. Sci.* USA. 86(4): 1173-7; Mizobuchi et al., 1993, *Biotechniques* 15(2):214-6; Ohara et al., 1989, *Proc. Natl. Acad. Sci.* USA. 86(15):5673-7; Walker et al., 1992, *Proc. Natl. Acad. Sci.* USA. 89(1):392-6; Zhang et al., 1997, *Methods Mol. Biol.* 69:61-87; EP0329822; WO 88/10315; WO 89/06700), transcription, reverse transcription, translation, single-nucleotide polymorphism analysis, and sequencing (e.g., shot gun sequencing, directed sequencing, sequencing by synthesis, pyrosequencing (see, e.g., U.S. Pat. Nos. 6,210,891, 6,258,568, and 6,274, 320), cycle sequencing, dideoxy or chain termination sequencing (see, e.g., Sanger et al., 1997, *Proc. Nat. Acad. Sci.* USA 74:5463) etc.). However, the skilled artisan will appreciate that reactions can occur in any type of reaction compartment, i.e., are not exclusively restricted to any type of reaction compartment. In addition, a reaction that can occur within any type of reaction compartment in some embodiments, may occur outside a reaction compartment as selected at the discretion of the practitioner.

For example, in some embodiments, analysis of one or a plurality of target polynucleotides can include amplification by PCR, including RT-PCR, which can be exponential, linear, asymmetric, and/or log-linear (see, e.g., U.S. Ser. No. 60/584, 665). In some embodiments, PCR amplification conditions can be designed for the amplification to plateau. By "plateau" herein is meant the stage of an amplification reaction (e.g., PCR) when synthesis and consequent accumulation of amplicons may terminate even though primers, template, polymerase and dNTPs can be present because hybridization of the first and second strands of double-stranded amplicons to each other out competes the hybridization of the amplification primers to the individual amplicon strands. A plateau also can be reached when one or more reagents are consumed (see, e.g., Saunders, *Quantitative Real-Time PCR* 106, 108 (Edwards et al. eds., 2004 (Horizon Bioscience, Norfolk UK, ISBN 0-9545232-7-X); and Bustin et al., *Analysis of mRNA Expression by Real-Time PCR* 127 (Edwards et al. eds., 2004 (Horizon Bioscience, Norfolk UK, ISBN 0-9545232-7-X). However, in some embodiments, amplification conditions can be designed to terminate before a reaction would otherwise reach a plateau. In some embodiments, terminating amplification before reaching a plateau can minimize over representation of target polynucleotides that are most abundant in a sample. Therefore, in some embodiments, an equivalent number of amplicons from each target polynucleotide can be produced irrespective of the starting copy number of each target polynucleotide. In some embodiments, terminating a PCR reaction before a plateau can be achieved using a limiting and equivalent number of amplification primer pairs for each target polynucleotide to be analyzed.

For example, in some embodiments, analysis of one or a plurality of target polynucleotides can include amplification by PCR as described in U.S. Patent Application No. 2004175733. Thus, in some embodiments, highly complex mixtures of target polynucleotides can be amplified in a standard multi-plex format, however, the conditions of the reaction can vary from conventional reactions. For example, in some embodiments, the concentration of thermostable polymerase, such as, AMPLITAQ GOLD™ DNA polymerase (Applied Biosystems, Applera Corp., Foster City, Calif.) can be from about 2 U/20 µl to about 16 U/20 µl, from about 2 U/20 µl to about 9 U/20 µl, from about 2 U/20 µl to about 6 U/20 µl, from about 7 U/20 µl to about 16 U/20 µl, or from about 2, 3, 4, 5, 6, 7, 8, 9, 10, 11, 12, 13, 14, 15, or 16 U/20 µl reaction volume. In some embodiments, primer extension can be for about 2, 3, 4, 5, 6, 7, 8, 9, 10 min., or even longer. In some embodiments, amplification primers can be used at concentrations in the range of about 30-900 nM each primer. Different amplification primer pairs may be present at different concentrations within this range or, alternatively, some or all of the amplification primers may be present at approximately equimolar concentrations within this range. In some embodiments, at least some of the amplification primers, for example, approximately 10%, 25%, 35%, 50%, 60%, or more, can be present in approximately equimolar concentrations ranging from about 30 nM to about 100 nM each primer. In some embodiments, all of the amplification primers can be present at approximately equimolar concentrations in the range of about 30 nM to about 100 nM each primer. In some embodiments, all of the amplification primers can be present at concentrations of about 30, 40, 45, 50, 60, 70, 80, 90, 100, 200, 300, 400, 500, 600, 700, 800 or 900 nM each primer. In some embodiment, some or all of the amplification primers can be present in a concentration of about 45 nM each primer. The amplification primer concentrations discussed above can be used regardless of whether the target polynucleotide(s) being multiplex amplified are RNA or DNA. The reverse-transcription reaction of a multiplex RT-PCR amplification works well at the stated primer concentrations.

The number of amplification cycles performed may depend upon, among other factors, the degree of amplification desired, which may depend upon such factors as the amount of target polynucleotide sample to be amplified and/ or the intended downstream use of the multiplex amplification product. Accordingly, the number of cycles employed in can vary for different applications and will be apparent to those of skill in the art. For most applications, reactions carried out for 10 amplification cycles are expected to yield sufficient amplification product even when the sample is derived from 1 to a few cells, is present in very low copy number, and/or is present only as a single copy, regardless of the amount of sample required to perform the analysis. However, more or fewer amplification cycles may be employed. In certain embodiments the multiplex amplification is carried out for as many as 10, 11, 12, 13, 14, 15, 16, 17, 18, 19, 20, or more cycles. In some embodiments, amplification can be carried out for 2-12 cycles, inclusive, for 5-11 cycles, inclusive, or for up to 14 cycles.

In some embodiments, a target polynucleotide, including an amplicon derived therefrom, can be clonally amplified. "Clonal amplification" as used herein refers to amplification of a sequence from a single copy of a target polynucleotide. Therefore, each amplicon produced in a clonal amplification reaction can be traced directly or indirectly to the same target polynucleotide. In some embodiments, clonal amplification reactions can employ the same principals and methods of PCR, LCR, OLA, Qβ-replicase amplification, NASBA, rolling circle amplification, transcription and other amplification reactions as described above.

In some embodiments, one or more target polynucleotide isolated in individual reaction compartments can be clonally amplified in parallel. "Isolated" target polynucleotide and "isolated" target sequence refer to a single copy of a target polynucleotide or sequence within a reaction compartment. Individual target polynucleotides in a sample can be isolated in individual reaction compartments by diluting the sample which can be used to prepare an inverse emulsion or microcapsules. In some embodiments, the diluted sample can be introduced directly into microcapsules. By diluting the target polynucleotides, the probability of having two or more target polynucleotides per reaction compartment can be substantially reduced. Thus, for some embodiments of clonal amplification, reaction mixture contain on average <1 target polynucleotide per reaction compartment.

In some embodiments, one or more amplification primers may be designed to amplify a target sequence and to introduce into one or more amplicons one or more sequences that are utilized for downstream analysis as described below. Therefore, the skilled artisan will appreciate that in some embodiments primer sequences introduced into an amplicon may be used for the manipulation, detection and/or analysis of target polynucleotides and accordingly may be used in sequences of other primers, probes, templates and the like. In some embodiments, the sequence introduced into the amplicon may be a code sequence which may be used as a surrogate or marker for each amplicon. By "code sequence" is meant a sequence of continuous nucleotides that is substantially unique. "Substantially unique" refers to a sequence suitable to identify or distinguish the polynucleotide comprising the code sequence. In some embodiments, code sequences may be used to identify the amplification product of a specific primer (see, e.g., U.S. Ser. Nos. 60/584,596; 60/584,621; 60/584,643; 60/584,665). In some embodiments, a sequence introduced into an amplicon may be shared by at least one other amplicon. In non-limiting exemplary embodiments, a "shared sequence" may be common to each forward amplification primer or each reverse amplification primer. Thus, "forward universal sequence" and "reverse universal sequence" refer to a primer sequence that is shared by each forward or reverse primer, respectively, of continuous nucleotides that is a region of diversity in comparison to a target sequence. In some embodiments, a sequence can be a universal sequence and can be shared by all amplification primers in a reaction mixture. In some embodiments, a sequence introduced into an amplicon can have one or more functions, such as, an enhancer, a promoter, restriction endonuclease site, etc. Amplification primers and methods for incorporating various types of sequences into amplification primers and amplicons derived therefrom are known in the art (see, e.g., U.S. Pat. Nos. 5,314,809, 5,853,989, 5,882,856, 6,090,552, 6,355,431, 6,617,138, 6,630,329, 6,635,419, 6,670,130, 6,670,161; and Weighardt et al., 1993, PCR Methods and App. 3:77, the disclosures of which are incorporated by reference).

In some embodiments, code, universal, and/or other types of sequences can be added to a target polynucleotide, including amplicons derived therefrom, by linkers and/or adaptors. (Sambrook et al., Molecular Cloning: A Laboratory Manual 1.84, 1.88-1.89, 1.98-1.102, 1.160-1.161, 11.20-11.21, 11.51-11.55, 11.102 (3d. ed. Cold Spring Harbor Laboratory Press), U.S. Pat. No. 5,674,743). For example, in some embodiments, a target polynucleotide can be sheared and/or restriction enzyme digested and/or treated with a polymerase or kinase to prepare the termini of the target polynucleotide for the addition of linkers and/or adaptors. In some embodiments, sequences can be added to a target polynucleotide by homologous recombination using RecA and/or other recombinases (see, e.g., U.S. Pat. Nos. 4,888,274, 5,989,879, 6,090, 539, 6,074,853, 6,200,812, 6,391,564, 6,524,856).

Determining the number, type, length, and composition of the various sequences of an amplification primer, including a target polynucleotide specific sequence, and linkers and their distribution or commonality among the various polynucleotides employed in the disclosed methods are within the capabilities of the ordinary skilled artisan.

In some embodiments, target polynucleotides, including amplicons derived therefrom, can be analyzed in parallel within individual reaction compartments by virtually any method selected at the discretion of the practitioner. Therefore, reactions comprising any one or more steps of probe or primer hybridization, primer extension, labeling, etc. can be used to detect, quantitate, and/or determine the composition of clonally amplified target polynucleotides.

For example, in some embodiments, target polynucleotides, including amplicons derived therefrom, can be sequenced in parallel using sequencing techniques based on sequencing-by-synthesis techniques. For example, in some embodiments the enzymatic method of Sanger et al. 1977, Proc. Natl. Acad. Sci., 74: 5463-5467, can be employed. The Sanger technique uses controlled synthesis of nucleic acids to generate fragments that terminate at specific points along the sequence of interest. Techniques based on the Sanger method typically begin by annealing a synthetic sequencing primer to a nucleic acid template (e.g., target polynucleotide or amplicon). The primer can be extended in the presence of four dNTPs (i.e., dGTP, dCTP, dATP and dTTP) and small proportion of four 2',3'-ddNTPs that carry a 3'-H atom on the deoxyribose moiety, rather than the conventional 3'-OH group. Incorporation of a ddNTP molecule into the growing DNA chain prevents formation of a phosphodiester bond with the succeeding dNTP, thus, extension of the growing chain can be terminated. The products of the reaction are a population or nested set of oligonucleotide chains with co-terminal 5' termini and whose lengths are determined by the distance between the 5' terminus of the primer used to initiate DNA synthesis and the sites of ddNTP chain termination. These populations of oligonucleotides can be separated by electrophoresis and the sequence of the template DNA determined (see, e.g., U.S. Pat. Nos. 4,994,372, 5,332,666, 5,498,523, 5,800,996, 5,821,058, 5,863,727, 5,945,526, and 6,258,568; Sanger et al., 1977, *Proc. Natl. Acad. Sci. USA,* 74: 5463-5467; and Sanger, 1981, *Science,* 214: 1205-1210).

Based on the labeling strategy used to identify the bases, described below, a sequencing reactions can be performed in parallel within each reaction compartment. For example, in some embodiments distinguishable labels can be attached to each ddNTP. Therefore, a single extension/termination reaction can be used which contains the four ddNTPs, each comprising a spectrally resolvable label. Suitable spectrally resolvable labels include but are not limited fluorophores. (see, e.g., U.S. Pat. Nos. 5,821,058, 5,332,666, and 5,945, 526.

In some embodiments, a method of sequencing based on the detection of base incorporation by the release of a pyrophosphate and simultaneous enzymatic nucleotide degradation is used (see, e.g., U.S. Pat. Nos. 6,210,891, 6,274,320, 6,258,568; Ronaghi et al., 1998, *Science* 281:363, 365). In these embodiments, a target polynucleotides in individual reaction compartments can be sequenced using a primer and adding four different dNTPs or ddNTPs to the reaction compartments subjected to a polymerase reaction. As each dNTP or ddNTP is added to the primer extension product, a pyrophosphate molecule is released. Pyrophosphate release can be detected enzymatically, such as, by the generation of light in a luciferase-luciferin reaction (see, e.g., WO 93/23564 and WO 89/09283). Additionally, a nucleotide degrading enzyme, such as apyrase, can be present during the reaction in order to degrade unincorporated nucleotides (see, e.g., U.S. Pat. No. 6,258,568; hereby incorporated by reference in its entirety). In other embodiments, the reaction can be carried out in the presence of a sequencing primer, polymerase, a nucleotide degrading enzyme, deoxynucleotide triphosphates, and a pyrophosphate detection system comprising ATP sulfurylase and luciferase (see, e.g., U.S. Pat. No. 6,258, 568).

In some embodiments, a method of sequencing can be fluorescent in situ sequencing (FISSEQ). In FISSEQ, a primer can be extended by adding a fluorescently-labeled dNTP followed by washing away of unincorporated dNTP. The incorporated dNTP is detected by fluorescence. At each cycle, the fluorescence from previous cycles can be "bleached" or digitally subtracted. (Mitra et al., 2003, *Analytical Biochemistry* 320:55-65; Zhu et al., 2003, *Science* 301:836-8; U.S. Application Nos. 20020120126, 20020120127, 20020127552, 20030099972, 20030124594, and 20030207265). In some embodiments, a method of sequencing can be hybridization sequencing (see, e.g., Baines et al., 1988, *J. Theor. Biol.* 135(3):303-7; Drmanac et al., *Genomics* 4(2):114-28; Khrapko et al., 1989, *FEBS Lett.* 256(1-2):118-22; Lysov et al., 1988, *Dokl AkadNauk SSSR.* 303(6):1508-11; Pevzner, 1989, *J. Biomol. Struct. Dyn.* 7(1): 63-73); Southern et al., 1992, *Genomics* 13(4):1008-17).

A variety of nucleic acid polymerases may be used in the methods described herein. For example, the nucleic acid polymerizing enzyme can be a thermostable polymerase or a thermally degradable polymerase. Suitable thermostable polymerases include, but are not limited to, polymerases isolated from *Thermus aquaticus, Thermus thermophilus, Pyrococcus woesei, Pyrococcus furiosus, Thermococcus litoralis,* and *Thermotoga maritima.* Therefore, in some embodiments, "cycle sequencing" can be performed. Suitable thermodegradable polymersases include, but are not limited to, *E. coli* DNA polymerase I, the Klenow fragment of *E. coli* DNA polymerase I, T4 DNA polymerase, T5 DNA polymerase, T7 DNA polymerase, and others. Examples of other polymerizing enzymes that can be used in the methods described herein include T7, T3, SP6 RNA polymerases and AMV, M-MLV and HIV reverse transcriptases.

Non-limiting examples of commercially available polymerases that can be used in the methods described herein include, but are not limited to, TaqFS®, AmpliTaq CS (Perkin-Elmer), AmpliTaq FS (Perkin-Elmer), Kentaq1 (AB Peptide, St. Louis, Mo.), Taquenase (ScienTech Corp., St. Louis, Mo.), ThermoSequenase (Amersham), Bst polymerase, VentR(exo⁻) DNA polymerase, Reader™Taq DNA polymerase, VENT™ DNA polymerase (New England Biolabs), DEEP-VENT™ DNA polymerase (New England Biolabs), PFU-Turbo™ DNA polymerase (Stratagene), Tth DNA polymerase, KlenTaq-1 polymerase, SEQUENASE™ 1.0 DNA polymerase (Amersham Biosciences), and SEQUENASE 2.0 DNA polymerase (United States Biochemicals).

For example, in some embodiments, target polynucleotides, including amplicons derived therefrom, can be sequenced using commercially available kits including but not limiting to ABI PRISM(T BigDye™ Terminator Cycle Sequencing Kits (Applied Biosystems, Foster City, Calif., see, e.g., Application Note 106AP05-01; Product Bulletins 106PB03-01 and 106PB09-01; Miscellaneous 106184 and 106185), DYEnamic™ ET Terminator Cycle Sequencing Kits (Amersham Biosciences Corp., Piscataway, N.J.), CEQ™2000 Dye Terminator Cycle Sequencing Chemistry (Beckman Coulter, Inc., Fullerton, Calif.), and other four color terminator sequencing systems.

The products of the sequencing reaction can be analyzed by a wide variety of methods. For example, the products can be separated by a size-dependent process, e.g., gel electrophoresis, capillary electrophoresis (CE: e.g., 3730 DNA Analyzer, 3730x1 DNA Analyzer, 3100-Avant genetic analyser, and 270A-HT Capillary Electrophoresis system (Applied Biosystems, Foster City, Calif.)) or chromatography, thin layer chromatography, or paper chromatography. The separated fragments can be detected, e.g., by laser-induced fluorescence (see, e.g., U.S. Pat. Nos. 5,945,526, 5,863,727, 5,821,058, 5,800,996, 5,332,666, 5,633,129, and 6,395,486), autoradiagraphy, or chemiluminescence. In some embodiments, the products of the sequencing reaction can be separated using gel electrophoresis and visualized using stains such as ethidium bromide or silver stain. The reaction products can also be analyzed by mass spectrometric methods (see, e.g., U.S. Pat. Nos. 6,225,450 and 510,412). In some embodiments, products of the sequencing reaction can be analyzed using microfluidic systems, including but not limited to microcapillary electrophoretic systems and methods (see, e.g., Doherty et al., 2004, *Analytical Chemistry* 76:5249-5256; Ertl et al., 2004, *Analytical Chemistry* 76:3749-3755; Haab et al., 1999, *Analytical Chemistry* 71:5137-5145 (1999); Kheterpal et al., 1999, *Analytical Chemistry* 71:31A-37A; Lagally et al., 2000, *Sensors and Actuators* B 63:138-146; Lagally et al., 2001, *Anal. Chem.* 73:565-570; Lagally et al., 2003, *Genetic Analysis Using a Portable PCR-CE Microsystem,* in *Micro Total Analysis Systems Vol.* 2, Northrup et al. (eds.) pp. 1283-1286; Liu et al., 1999, *Anal. Chem.* 71:566-573; Medintz et al., 2000, *Electrophoresis* 21:2352-2358; Medintz et al., 2001, *Genome Research* 11:413-421; Paegel et al., *Current Opinions in Biotechnology* 14:42-50; Scherer et al., 1999, *Electrophoresis* 20:1508-1517; Shi et al., 1999, *Analytical Chemistry* 71:5354-5361; Wedemayer et al., 2001, *BioTechniques* 30:122-128; U.S. Pat. Nos. 6,787,015, 6,787,016; U.S. Application Nos. 20020166768, 20020192719, 20020029968, 20030036080, 20030087300, 20030104466, 20040045827, 20040096960; EP1305615; and WO 02/08744).

In some embodiments, sequencing products can be separated and analyzed by capillary electrophoresis (see, e.g., U.S. Pat. Nos. RE37941, 5,384,024, 6,372,106, 6,372,484, 6,387,234, 6,387,236, 6,402,918, 6,402,919, 6,432,651, 6,462,816, 6,475,361, 6,476,118, 6,485,626, 6,531,041, 6,544,396, 6,576,105, 6,592,733, 6,596,140, 6,613,212, 6,635,164, and 6,706,162). In some embodiments, the sequencing products in the microcapsules can be injected into the capillary directly from the microcapsules. In various exemplary embodiments, a dielectric force can be used to locate a microcapsule at the CE tip, microcapsules can be captured on affinity pads or in wells with spacing matched to the capillary pitch, and microcapsules can be placed in a separation polymer (e.g., POP-4™ POP-6™, or POP-7™ (Applied Biosystems, Foster City, Calif.), linear polyacrylamide (LPA: Klepamik et al., 2001, *Electrophoresis* 22(4): 783-8; Kotler et al., 2002, *Electrophoresis* 23(17):3062-70; Manabe et al., 1998, *Electrophoresis* 19:2308-2316.) and the polymer/microcapsules suspension can be drawn to the CE tip at low pressure. Once a microcapsule it located at the capillary tip, in some embodiments, the sequencing products can be injected directly from the microcapsule by an electric field and/or by mechanically and/or chemically and/or enzymatically compromising the capsule wall.

The various primers (e.g., amplification and/or sequencing) suitable for use in the disclosed methods may be target sequence-specific or may be designed to hybridize to sequences that flank a target sequence to be analyzed. Thus, the actual nucleotide sequences of each primer may depend upon the target sequence and target polynucleotide, which will be apparent to those of skill in the art. Methods for designing primers suitable for amplifying target sequences of interest are well-known.

Generally, each primer should be sufficiently long to prime template-directed synthesis under the conditions of the selected reaction. The exact lengths of the primers may depend on many factors, including but not limited to, the desired hybridization temperature between the primers and polynucleotides, the complexity of the different target polynucleotide sequences, the salt concentration, ionic strength, pH and other buffer conditions, and the sequences of the primers and polynucleotides. The ability to select lengths and sequences of primers suitable for particular applications is within the capabilities of ordinarily skilled artisans (see, e.g., Sambrook et al. *Molecular Cloning: A Laboratory Manual* 9.50-9.51, 11.46, 11.50 (2d. ed., Cold Spring Harbor Laboratory Press); Sambrook et al., *Molecular Cloning: A Laboratory Manual* 10.1-10.10 (3d. ed. Cold Spring Harbor Laboratory Press)). In some embodiments, the primers contain from about 15 to about 35 nucleotides that are suitable for hybridizing to a target polynucleotide and form a substrate suitable for DNA synthesis, although the primers may contain more or fewer nucleotides. Shorter primers generally require lower temperatures to form sufficiently stable hybrid complexes with target sequences. The capability of polynucleotides to anneal can be determined by the melting temperature ("$T_m$") of the hybrid complex. $T_m$ is the temperature at which 50% of a polynucleotide strand and its perfect complement form a double-stranded polynucleotide. Therefore, the $T_m$ for a selected polynucleotide varies with factors that influence or affect hybridization. In some embodiments, in which thermocycling occurs, the primers can be designed to have a melting temperature ("$T_m$") in the range of about 60-75° C. Melting temperatures in this range tend to insure that the primers remain annealed or hybridized to the target polynucleotide at the initiation of primer extension. The actual temperature used for a primer extension reaction may depend upon, among other factors, for example, the concentration of the primers. For reactions carried out with a thermostable polymerase such as Taq DNA polymerase, in exemplary embodiments primers can be designed to have a $T_m$ in the range of about 60 to about 78° C. or from about 55 to about 70° C. The melting temperatures of the different primers can be different; however, in an alternative embodiment they should all be approximately the same, i.e., the $T_m$ of each primer, for example, in a parallel reaction can be within a range of about 5° C. or less. The $T_m$s of various primers can be determined empirically utilizing melting techniques that are well-known in the art (see, e.g., Sambrook et al. *Molecular Cloning: A Laboratory Manual* 11.55-11.57 (2d. ed., Cold Spring Harbor Laboratory Press)). Alternatively, the $T_m$ of a primer can be calculated. Numerous references and aids for calculating $T_m$s of primers are available in the art and include, by way of example and not limitation, Baldino et al. *Methods Enzymology*. 168:761-777; Bolton et al., 1962, *Proc. Natl. Acad. Sci.* USA 48:1390; Bresslauer et al., 1986, *Proc. Natl. Acad. Sci.* USA 83:8893-8897; Freier et al., 1986, *Proc. Natl. Acad. Sci.* USA 83:9373-9377; Kierzek et al., *Biochemistry* 25:7840-7846; Rychlik et al., 1990, *Nucleic Acids Res.* 18:6409-6412 (erratum, 1991, *Nucleic Acids Res.* 19:698); Rychlik. *J. NIH Res.* 6:78; Sambrook et al. *Molecular Cloning: A Laboratory Manual* 9.50-9.51, 11.46-11.49 (2d. ed., Cold Spring Harbor Laboratory Press); Sambrook et al., *Molecular Cloning: A Laboratory Manual* 10.1-10.10 (3d. ed. Cold Spring Harbor Laboratory Press)); Suggs et al., 1981, *In Developmental Biology Using Purified Genes* (Brown et al., eds.), pp. 683-693, Academic Press; Wetmur, 1991, *Crit. Rev. Biochem. Mol. Biol.* 26:227-259, which disclosures are incorporated by reference. Any of these methods can be used to determine a $T_m$ of a primer.

As the skilled artisan will appreciate, in general, the relative stability and therefore, the $T_m$s, of RNA:RNA, RNA:DNA, and DNA:DNA hybrids having identical sequences for each strand may differ. In general, RNA:RNA hybrids are the most stable (highest relative $T_m$) and DNA:DNA hybrids are the least stable (lowest relative $T_m$). Accordingly, in some embodiments, another factor to consider, in addition to those described above, when designing a primer is the structure of the primer and target polynucleotide. For example, in the embodiment in which an RNA polynucleotide is reverse transcribed to produce a cDNA, the determination of the suitability of a DNA primer for the reverse transcription reaction should include the effect of the RNA polynucleotide on the $T_m$ of the primer. Although the $T_m$s of various hybrids may be determined empirically, as described above, examples of methods of calculating the $T_m$ of various hybrids are found at Sambrook et al. *Molecular Cloning: A Laboratory Manual* 9.51 (2d. ed., Cold Spring Harbor Laboratory Press).

The sequences of primers useful for the disclosed methods are designed to be substantially complementary to regions of the target polynucleotides. By "substantially complementary" herein is meant that the sequences of the primers include enough complementarity to hybridize to the target polynucleotides at the concentration and under the temperature and conditions employed in the reaction and to be extended by the DNA polymerase.

Figure 2:
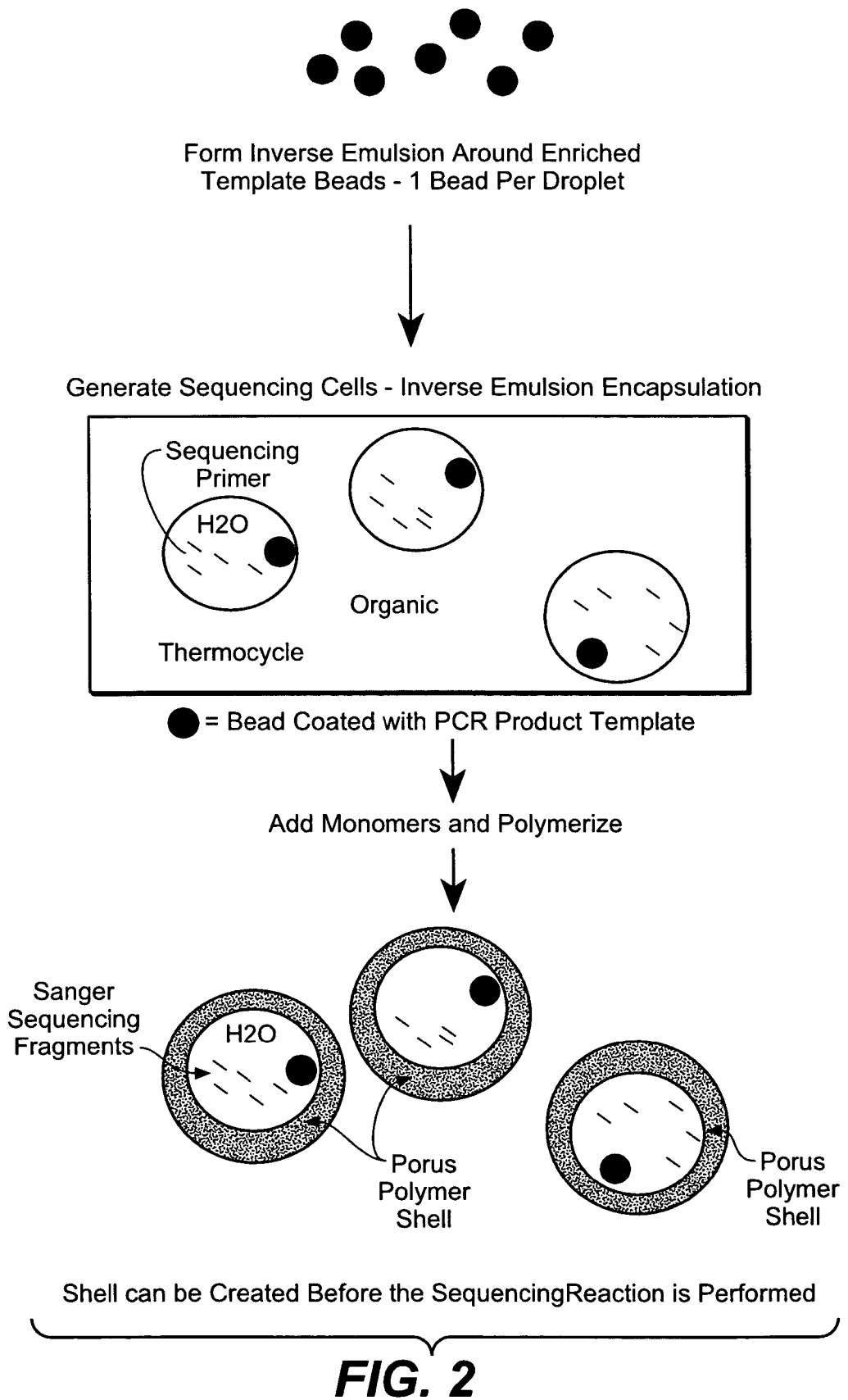
FIG. 2 illustrates an embodiment of sequencing amplicons attached to a microparticle in a microcapsule.
Figure 3:
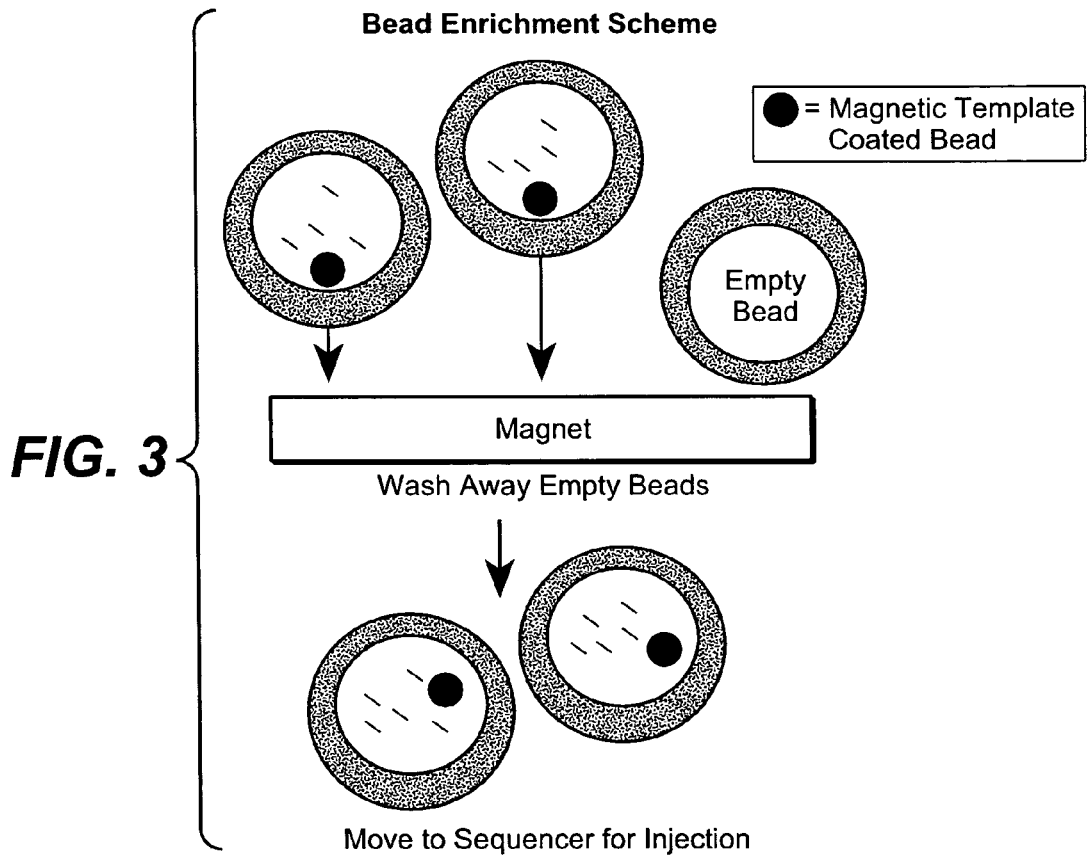
FIG. 3 illustrates an embodiment of positively selecting for microcapsules comprising microparticles that are magnetically labeled.
Figure 4:
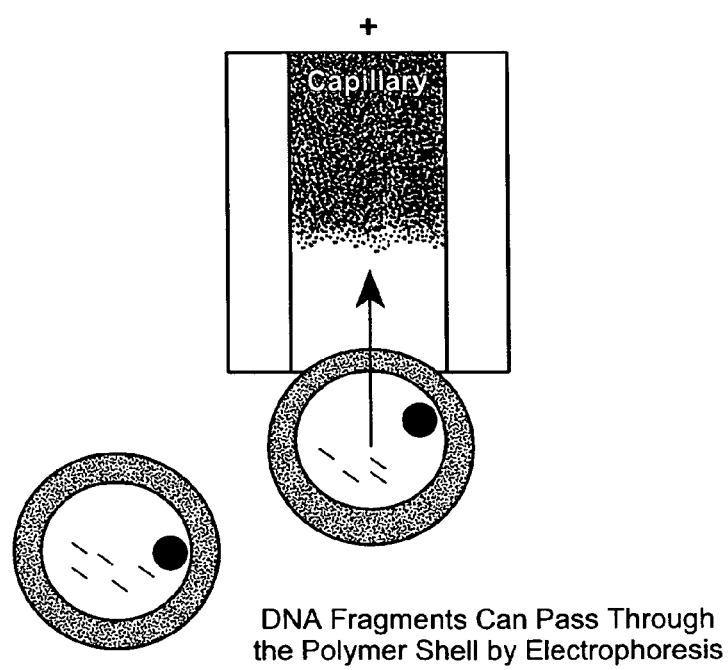
FIG. 4 illustrates an embodiment of locating a microcapsule comprising sequencing reaction on the tip of a capillary electrophoresis apparatus.
Figure 5:
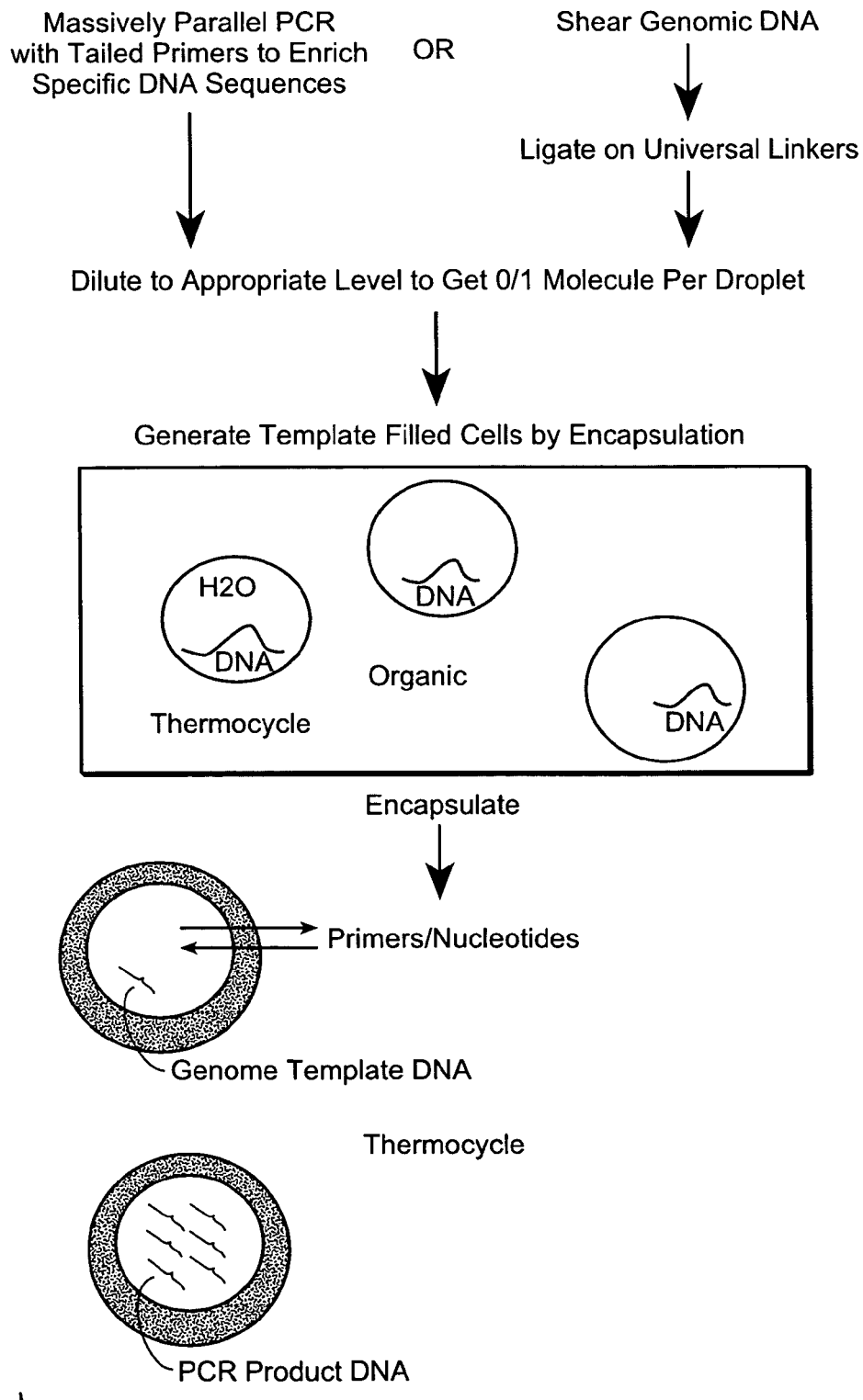
FIG. 5 illustrates an embodiment an embodiment of isolated a genomic DNA target polynucleotide in a microcapsule for amplification by PCR.
Figure 6:
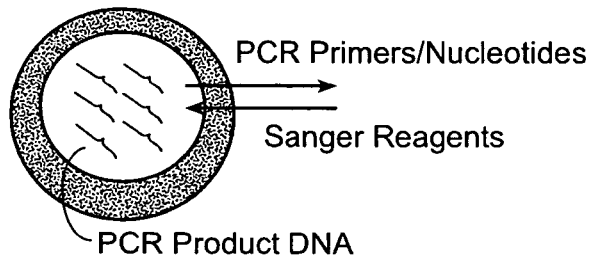
FIG. 6 illustrates an embodiment of sequencing clonally amplified amplicons in a microcapsule and an embodiment of adjusting the size of the pores in a microcapsule.
Figure 6:
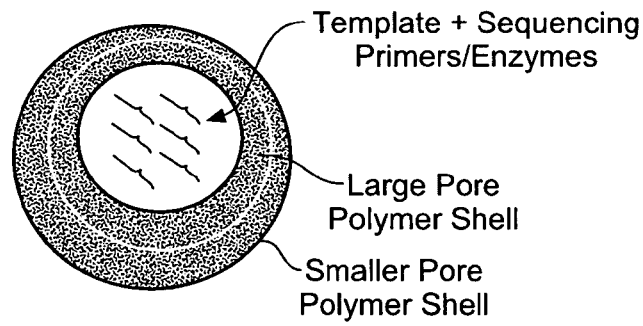
Figure 6:
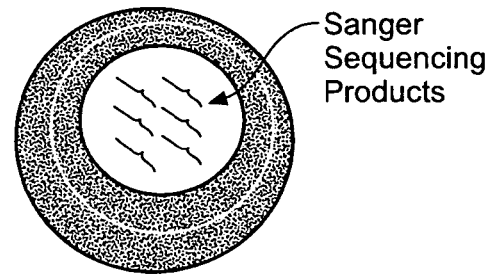
Figure 7:
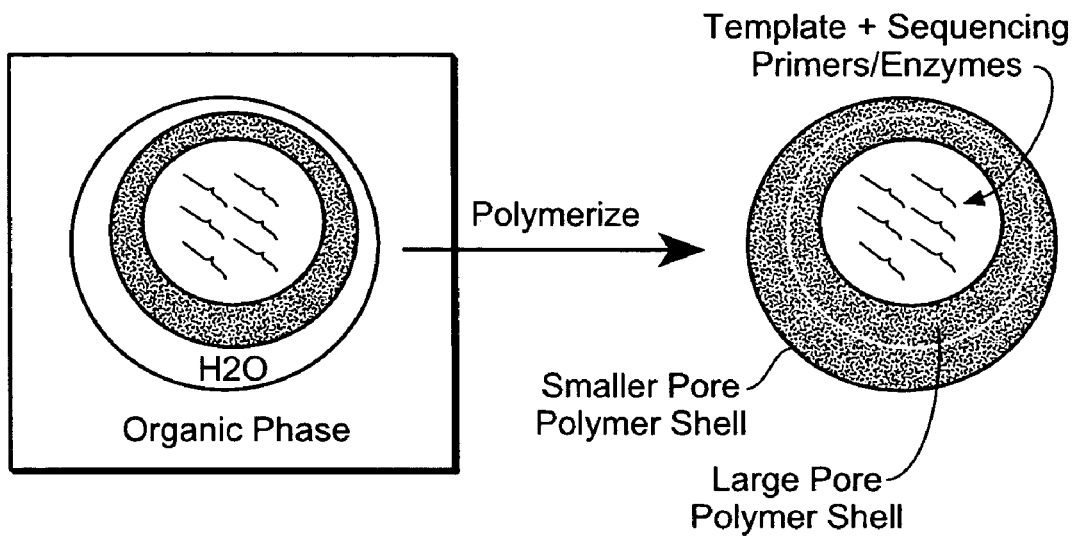
FIG. 7 illustrates embodiments of adjusting the size of the pores in microcapsules.
Figure 7:
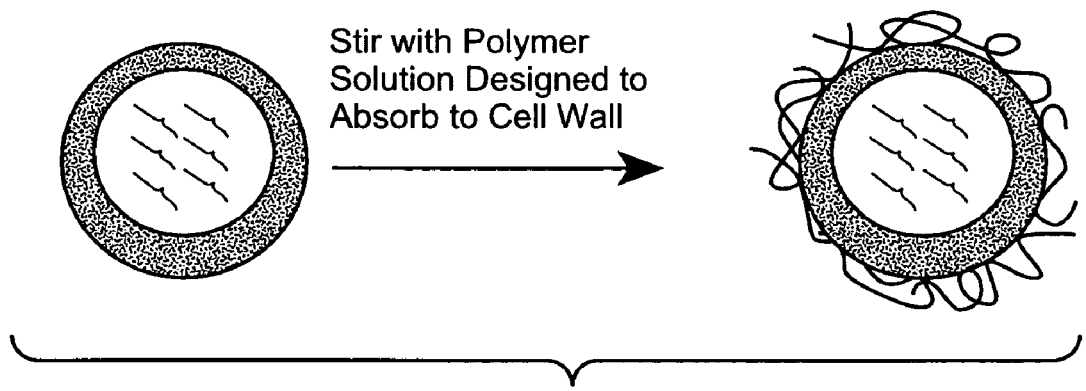

In some embodiments, amplification and sequencing primers can be a nucleobase polymer. By "nucleobase" is meant naturally occurring and synthetic heterocyclic moieties commonly known to those who utilize nucleic acid or polynucleotide technology or utilize polyamide or peptide nucleic acid technology to generate polymers that can hybridize to polynucleotides in a sequence-specific manner. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobases include those nucleobases disclosed in FIGS. 2(A) and 2(B) of Buchardt et al. (U.S. Pat. No. 6,357,163, WO 92/20702 and WO 92/20703).

Nucleobases can be linked to other moieties to form nucleosides, nucleotides, and nucleoside/tide analogs. As used herein, "nucleoside" refers to a compound consisting of a purine, deazapurine, or pyrimidine nucleoside base, e.g., adenine, guanine, cytosine, uracil, thymine, 7-deazaadenine, 7-deazaguanosine, that is linked to the anomeric carbon of a pentose sugar at the 1' position, such as a ribose, 2'-deoxyribose, or a 2',3'-di-deoxyribose. When the nucleoside base is purine or 7-deazapurine, the pentose is attached at the 9-position of the purine or deazapurine, and when the nucleoside base is pyrimidine, the pentose is attached at the 1-position of the pyrimidine (see, e.g., Komberg and Baker, DNA Replication, 2nd Ed. (Freeman 1992)). The term "nucleotide" as used herein refers to a phosphate ester of a nucleoside, e.g., a mono-, a di-, or a triphosphate ester, wherein the most common site of esterification is the hydroxyl group attached to the C-5 position of the pentose. "Nucleotide 5'-triphosphate" refers to a nucleotide with a triphosphate ester group at the 5' position. The term "nucleoside/tide" as used herein refers to a set of compounds including both nucleosides and/or nucleotides.

"Nucleobase polymer or oligomer" refers to two or more nucleobases connected by linkages that permit the resultant nucleobase polymer or oligomer to hybridize to a polynucleotide having a complementary nucleobase sequence. Nucleobase polymers or oligomers include, but are not limited to, poly- and oligonucleotides (e.g., DNA and RNA polymers and oligomers), poly- and oligonucleotide analogs and poly- and oligonucleotide mimics, such as polyamide or peptide nucleic acids. Nucleobase polymers or oligomers can vary in size from a few nucleobases, from 2 to 40 nucleobases, to several hundred nucleobases, to several thousand nucleobases, or more.

"Polynucleotide or oligonucleotide" refers to nucleobase polymers or oligomers in which the nucleobases are connected by sugar phosphate linkages (sugar-phosphate backbone). Exemplary poly- and oligonucleotides include polymers of 2'-deoxyribonucleotides (DNA) and polymers of ribonucleotides (RNA). A polynucleotide may be composed entirely of ribonucleotides, entirely of 2'-deoxyribonucleotides or combinations thereof.

In some embodiments, a nucleobase polymer is an polynucleotide analog or an oligonucleotide analog. By "polynucleotide analog or oligonucleotide analog" is meant nucleobase polymers or oligomers in which the nucleobases are connected by a sugar phosphate backbone comprising one or more sugar phosphate analogs. Typical sugar phosphate analogs include, but are not limited to, sugar alkylphosphonates, sugar phosphoramidites, sugar alkyl- or substituted alkylphosphotriesters, sugar phosphorothioates, sugar phosphorodithioates, sugar phosphates and sugar phosphate analogs in which the sugar is other than 2'-deoxyribose or ribose, nucleobase polymers having positively charged sugarguanidyl interlinkages such as those described in U.S. Pat. No. 6,013,785 and U.S. Pat. No. 5,696,253 (see also, Dagani, 1995, Chem. & Eng. News 4-5:1153; Dempey et al., 1995, J. Am. Chem. Soc. 117:6140-6141). Such positively charged analogues in which the sugar is 2'-deoxyribose are referred to as "DNGs," whereas those in which the sugar is ribose are referred to as "RNGs." Specifically included within the definition of poly- and oligonucleotide analogs are locked nucleic acids (LNAs; see, e.g., Elayadi et al., 2002, Biochemistry 41:9973-9981; Koshkin et al., 1998, J. Am. Chem. Soc. 120: 13252-3; Koshkin et al., 1998, Tetrahedron Letters, 39:4381-4384; Jumar et al., 1998, Bioorganic & Medicinal Chemistry Letters 8:2219-2222; Singh and Wengel, 1998, Chem. Commun., 12:1247-1248; WO 00/56746; WO 02/28875; and, WO 01/48190.

In some embodiments, a nucleobase polymer is a polynucleotide mimic or oligonucleotide mimic. "Polynucleotide mimic or oligonucleotide mimic" refers to a nucleobase polymer or oligomer in which one or more of the backbone sugar-phosphate linkages is replaced with a sugar-phosphate analog. Such mimics are capable of hybridizing to complementary polynucleotides or oligonucleotides, or polynucleotide or oligonucleotide analogs or to other polynucleotide or oligonucleotide mimics, and may include backbones comprising one or more of the following linkages: positively charged polyamide backbone with alkylamine side chains as described in U.S. Pat. Nos. 5,786,461, 5,766,855, 5,719,262, 5,539,082 and WO 98/03542 (see also, Haaima et al., 1996, Angewandte Chemie Int'l Ed. in English 35:1939-1942; Lesnick et al., 1997, Nucleotid. 16:1775-1779; D'Costa et al., 1999, Org. Lett. 1:1513-1516; Nielsen, 1999, Curr. Opin. Biotechnol. 10:71-75); uncharged polyamide backbones as described in WO 92/20702 and U.S. Pat. No. 5,539,082; uncharged morpholino-phosphoramidate backbones as described in U.S. Pat. Nos. 5,698,685, 5,470,974, 5,378,841, and 5,185,144 (see also, Wages et al., 1997, BioTechniques 23:1116-1121); peptide-based nucleic acid mimic backbones (see, e.g., U.S. Pat. No. 5,698,685); carbamate backbones (see, e.g., Stirchak and Summerton, 1987, J. Org. Chem. 52:4202); amide backbones (see, e.g., Lebreton, 1994, Synlett. February, 1994:137); methylhydroxylamine backbones (see, e.g., Vasseur et al., 1992, J. Am. Chem. Soc. 114:4006); 3'-thioformacetal backbones (see, e.g., Jones et al., 1993, J. Org. Chem. 58:2983) and sulfamate backbones (see, e.g., U.S. Pat. No. 5,470,967). All of the preceding references are herein incorporated by reference.

"Peptide nucleic acid" or "PNA" refers to poly- or oligonucleotide mimics in which the nucleobases are connected by amino linkages (uncharged polyamide backbone) such as described in any one or more of U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470, 6,451,968, 6,441,130, 6,414,112 and 6,403,763; all of which are incorporated herein by reference. The term "peptide nucleic acid" or "PNA" shall also apply to any oligomer or polymer comprising two or more subunits of those polynucleotide mimics described in the following publications: Lagriffoul et al., 1994, Bioorganic & Medicinal Chemistry Letters, 4:1081-1082; Petersen et al., 1996, Bioorganic & Medicinal Chemistry Letters, 6:793-796; Diderichsen et al., 1996, Tett. Lett. 37:475-478; Fujii et al., 1997, Bioorg. Med. Chem. Lett. 7:637-627; Jordan et al., 1997, Bioorg. Med. Chem. Lett. 7:687-690; Krotz et al., 1995, Tett. Lett. 36:6941-6944; Lagriffoul et al., 1994, Bioorg. Med. Chem. Lett. 4:1081-1082; Diederichsen, 1997, Bioorg. Med. Chem. 25 Letters, 7:1743-1746; Lowe et al., 1997, J. Chem. Soc. Perkin Trans. 1, 1:539-546; Lowe et al., 1997, J. Chem. Soc. Perkin Trans. 11:547-554; Lowe et al., 1997, I. Chem. Soc. Perkin Trans. 1 1:555-560; Howarth et al., 1997, I. Org. Chem. 62:5441-5450; Altmann et al., 1997, Bioorg. Med. Chem. Lett., 7:1119-1122; Diederichsen, 1998, Bioorg. Med. Chem. Lett., 8:165-168; Diederichsen et al., 1998, *Angew. Chem. mt. Ed.*, 37:302-305; Cantin et al., 1997, *Tett. Lett.*, 38:4211-4214; Ciapetti et al., 1997, *Tetrahedron*, 53:1167-1176; Lagriffoule et al., 1997, *Chem. Eur. 1.* 3:912-919; Kumar et al., 2001, *Organic Letters* 3(9):1269-1272; and the Peptide-Based Nucleic Acid Mimics (PENAMs) of Shah et al. as disclosed in WO 96/04000.

Some examples of PNAs are those in which the nucleobases are attached to an N-(2-aminoethyl)-glycine backbone, i.e., a peptide-like, amide-linked unit (see, e.g., U.S. Pat. No. 5,719,262; Buchardt et al., 1992, WO 92/20702; Nielsen et al., 1991, *Science* 254:1497-1500).

In some embodiments, a nucleobase polymer is a chimeric oligonucleotide. By "chimeric oligonucleotide" is meant a nucleobase polymer or oligomer comprising a plurality of different polynucleotides, polynucleotide analogs and polynucleotide mimics. For example a chimeric oligo may comprise a sequence of DNA linked to a sequence of RNA. Other examples of chimeric oligonucleotides include a sequence of DNA linked to a sequence of PNA, and a sequence of RNA linked to a sequence of PNA.

In some embodiments, various components of the disclosed methods, including but not limited to primers, ddNTPs, and the reaction compartments, can comprise a detectable moiety. "Detectable moiety," "detection moiety" or "label" refer to a moiety that renders a molecule to which it is attached detectable or identifiable using known detection systems (e.g., spectroscopic, radioactive, enzymatic, chemical, photochemical, biochemical, immunochemical, chromatographic, physical (e.g., sedimentation, centrifugation, density), electrophoretic, gravimetric, or magnetic systems). Non-limiting examples of labels include quantum dots, isotopic labels (e.g., radioactive or heavy isotopes), magnetic labels; spin labels, electric labels; thermal labels; colored labels (e.g., chromophores), luminescent labels (e.g., fluorescers, chemiluminescers), enzyme labels (e.g., horseradish peroxidase, alkaline phosphatase, luciferase, β-galactosidase) (Ichiki et al., 1993, *J. Immunol.* 150(12):5408-5417; Nolan et al., 1988, *Proc. Natl. Acad. Sci.* USA 85(8):2603-2607)), antibody labels, and chemically modifiable labels. In addition, in some embodiments, such labels include components of ligand-binding partner pairs (e.g., antigen-antibody (including single-chain antibodies and antibody fragments, e.g., FAb, F(ab)'$_2$, Fab', Fv, etc. (*Fundamental Immunology* 47-105 (William E. Paul ed., 5$^{th}$ ed., Lippincott Williams & Wilkins 2003)), hormone-receptor binding, neurotransmitter-receptor binding, polymerase-promoter binding, substrate-enzyme binding, inhibitor-enzyme binding (e.g., sulforhodamine-valyl-alanyl-aspartyl-fluoromethylketone (SR-VAD-FMK-caspase(s) binding), allosteric effector-enzyme binding, biotin-streptavidin binding, digoxin-antidigoxin binding, carbohydrate-lectin binding, Annexin V-phosphatidylserine binding (Andree et al., 1990, *J. Biol. Chem.* 265(9): 4923-8; van Heerde et al., 1995, *Thromb. Haemost.* 73(2): 172-9; Tait et al., 1989, *J. Biol. Chem.* 264(14):7944-9), nucleic acid annealing or hybridization, or a molecule that donates or accepts a pair of electrons to form a coordinate covalent bond with the central metal atom of a coordination complex. In various exemplary embodiments the dissociation constant of the binding ligand can be less than about $10^{-4}$-$10^{-6}$ M$^{-1}$, less than about $10^{-5}$ to $10^{-9}$ M$^{-1}$, or less than about $10^{-7}$-$10^{-9}$ M$^{-1}$.

"Fluorescent label," "fluorescent moiety," and "fluorophore" refer to a molecule that may be detected via its inherent fluorescent properties. Examples of suitable fluorescent labels include, but are not limited to, fluorescein, rhodamine, tetramethylrhodamine, eosin, erythrosin, coumarin, methylcoumarins, pyrene, Malachite Green, stilbene, Lucifer Yellow, Cascade BlueJ, Texas Red, IAEDANS, EDANS, BODIPY FL, LC Red 640, phycoerythrin, LC Red 705, Oregon green, Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE), FITC, Rhodamine, Texas Red (Pierce, Rockford, Ill.), Cy5, Cy5.5, Cy7 (Amersham Life Science, Pittsburgh, Pa.) and tandem conjugates, such as but not limited to, Cy5PE, Cy5.5PE, Cy7PE, Cy5.5APC, Cy7APC. In some embodiments, suitable fluorescent labels also include, but are not limited to, green fluorescent protein (GFP; Chalfie et al., 1994, *Science* 263(5148):802-805), EGFP (Clontech Laboratories, Inc., Palo Alto, Calif.), blue fluorescent protein (BFP; Quantum Biotechnologies, Inc. Montreal, Canada; Heim et al, 1996, *Curr. Biol.* 6:178-182; Stauber, 1998, *Biotechniques* 24(3):462-471), enhanced yellow fluorescent protein (EYFP; Clontech Laboratories, Inc., Palo Alto, Calif.), and renilla (WO 92/15673; WO 95/07463; WO 98/14605; WO 98/26277; WO 99/49019; U.S. Pat. Nos. 5,292,658, 5,418,155, 5,683,888, 5,741,668, 5,777,079, 5,804,387, 5,874,304, 5,876,995, and 5,925,558). Further examples of fluorescent labels are found in Haugland, *Handbook of Fluorescent Probes and Research, 9$^{th}$* Edition, Molecule Probes, Inc. Eugene, Oreg. (ISBN 0-9710636-0-5).

In some embodiments, a label can be a microparticle. By "microparticle", "microsphere", "microbead", "bead" and grammatical equivalents herein are meant a small discrete particle synthesized from virtually any number of material(s). As known in the art, the composition of beads can vary depending on the type of assay in which they are used and, therefore, selecting a microbead composition is within the abilities of the practitioner. Suitable bead compositions include those used in peptide, nucleic acid and organic synthesis, including, but not limited to, plastics, ceramics, glass, methylstyrene, synthetic polymers (e.g., polystyrene, acrylic polymers), paramagnetic materials (U.S. Pat. Nos. 4,358,388, 4,654,267, 4,774,265, 5,320,944, 5,356,713), thoria sol, carbon graphite, titanium dioxide, latex or cross-linked dextrans such as SEPHAROSE™ and, SEPHADEX™, agarose, cellulose, including cellulose derivatives (e.g., carboxymethyl cellulose, hydroxyethyl cellulose), proteinaceous polymer, nylon, globulin, natural polymers (e.g., DNA), cross-linked micelles, and Teflon may all be used (see, e.g., *Microsphere Detection Guide* from Bangs Laboratories, Fishers, Ind.). Beads are also commercially available from, for example, Bio-Rad Laboratories (Richmond, Calif.), LKB (Sweden), Pharmacia (Piscataway, N.J.), IBF (France), Dynal Inc. (Great Neck, N.Y.). In some embodiments, beads may contain a cross-linking agent, such as, but not limited to divinyl benzene, ethylene glycol dimethacrylate, trimethylol propane trimethacrylate, N,N'methylene-bis-acrylamide, adipic acid, sebacic acid, succinic acid, citric acid, 1,2,3,4-butanetetracarboxylic acid, or 1,10 decanedicarboxylic acid or other functionally equivalent agents known in the art. In various exemplary embodiments, beads can be spherical, non-spherical, egg-shaped, irregularly shaped, and the like. The average diameter of a microparticle can be selected at the discretion of the practitioner. However, generally the average diameter of microparticle can range from nanometers (e.g. about 100 nm) to millimeters (e.g. about 1 mm), from about 0.2 μm to about 200 μm, from about 0.5 μm to about 10 μm, from about 2.0 μm to about 100 μm, from about 10 μm to about 80 μm, and from about 20 μm to about 40 μm, although in some embodiments smaller and larger beads may be used.

In some embodiments a microparticle can be porous, thus increasing the surface area available for attachment to another molecule, moiety, or compound (e.g., a primer). Thus, microparticles may have additional surface functional groups to facilitate attachment and/or bonding. These groups may include carboxylates, esters, alcohols, carbamides, carbodiimides, aldehydes, N-hydroxysuccinamide (NHS) reactive groups, amines, sulfur oxides, nitrogen oxides, or halides. Methods of attaching another molecule or moiety to a bead are known in the art (see, e.g., U.S. Pat. Nos. 6,268,222, 6,649,414). In some embodiments, a microparticle can further comprise a label.

In addition to providing a label, in some embodiments, microparticles can be used to transfer the contents of a reaction compartment to another reaction compartment for further analysis. For example, in some embodiments, multiple copies of an amplification primer can be attached to a microparticle. For example, when employed in a clonal amplification reaction in a reaction compartment, a microparticle with clonally amplified amplicons attached to its surface can be produced. The microparticles can be collect en masse and redistributed into individual reaction compartments for further analysis. For example, in some embodiments in which clonal amplification using an amplification primer attached to a microbead takes place in aqueous compartments of an inverse emulsion, the emulsion can be collapsed, the beads collected, and redistributed into a second emulsion or microcapsules. In some embodiments, microparticle with the highest number of surface amplicons can be purified from non- or poorly-coated beads by ion exchange, electrophoresis, dielectrophoresis, and/or fluorescence activated sorting. In some embodiments, the microparticle may comprise one or more labels to further facilitate analysis and manipulation of reaction compartments and their contents. For example, in some embodiments, a microparticle can comprise a magnetic label. Therefore, reaction compartments comprising a magnetic label can be positively selected for further analysis while reaction compartments that do not comprise a magnetic label can be discarded.

The compositions and reagents described herein can be packaged into kits. In some embodiments, a kit comprises a reagent for making a reaction mixture comprising one or more reaction compartments. In some embodiments, the reaction compartment can be used in conjunction with one or more reagents from commercially available kits, including, but not limited to, those available from Applied Biosystems (i.e., Big Dye® Terminator Cycle Sequencing Kit), Epicentre (i.e., SequiTherm™ Cycle Sequencing Kit), Amersham (i.e., DYEnamic Direct Dye-Primer Cycle Sequencing Kits), Boehringer Mannheim (i.e., CycleReader™ DNA Sequencing Kit), Bionexus Inc. (i.e., AccuPower DNA Sequencing Kit), and USB cycle sequencing kits (i.e., Thermo Sequenase™ Cycle Sequencing Kit).

In some embodiments, a kit can comprise one or a plurality of microparticles having primer suitable for amplifying one or more target polynucleotides. In some embodiments each primers can comprise a target specific sequence and/or a universal sequence. In some embodiments, the microparticles can further comprise various labels, including but not limited to, fluorescent and/or magnetic labels. In some embodiments, a kit can comprise a library of target nucleic acid sequences, wherein each target polynucleotide can be attached to an individual microparticle suitable for use in a reaction compartment. In some embodiments, a kit can comprise one or more reaction compartments comprising reagents suitable for performing a reaction selected at the discretion of a practitioner. For example, in some embodiments, a kit can comprise one or more reaction compartments comprising one more sequencing reagents.

The various components included in the kit are typically contained in separate containers, however, in some embodiments, one or more of the components can be present in the same container. Additionally, kits can comprise any combination of the compositions and reagents described herein. The kits described herein can comprise additional reagents that are necessary or may be optional for performing the disclosed methods. Such reagents include, but are not limited to, buffers, molecular size standards, control target polynucleotides, and the like.

In this application, the use of the singular includes the plural unless specifically stated otherwise. The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

All literature and similar materials cited in this application, including but not limited to, patents, patent applications, articles, books, treatises, and internet web pages, regardless of the format of such literature and similar materials, are expressly incorporated by reference in their entirety for any purpose. In the event that one or more of the incorporated literature and similar materials differs from or contradicts this application, including but not limited to defined terms, term usage, described techniques, or the like, this application controls.

What is claimed is:

1. A method of analyzing the contents of a microcapsule comprising inserting the microcapsule into a capillary of a capillary electrophoresis system, and analyzing one or more molecules released from the microcapsule in the capillary.

2. The method according to claim 1, wherein said molecules are produced by sequencing one or more polynucleotides contained within said microcapsule.

3. The method according to claim 1, wherein said one or more molecules are produced by sequencing one or more polynucleotides contained within an aqueous compartment of an inverse emulsion and said microcapsule is produced by encapsulating said compartment.

4. The method according to claim 2, wherein said sequencing is Sanger sequencing.

5. The method according to claim 2, wherein said one or more polynucleotides are attached to a surface.

6. The method according to claim 2, wherein said polynucleotides comprise amplicons produced by clonally amplifying a target polynucleotide.

7. The method according to claim 6, wherein said target polynucleotide is clonally amplified in a second microcapsule.

8. The method according to claim 6, wherein said target polynucleotide is clonally amplified in an aqueous compartment of an inverse emulsion.

9. The method according to claim 1, wherein said microcapsule comprises a hydrogel.

10. The method according to claim 1, wherein said microcapsule is a colloidosome.

11. The method according to claim 1, wherein said microcapsule is produced by layer-by-layer polymer deposition.

12. The method according to claim 1, wherein said microcapsule is produced by polymer precipitation.

13. A method of analyzing the contents of a plurality of microcapsules comprising inserting the plurality of microcapsules into a plurality of capillaries of an electrophoresis system, and analyzing the contents of the capsules.

14. A sequencing method comprising:
a) clonally amplifying a plurality of target polynucleotides in a plurality of aqueous compartments of an inverse emulsion, wherein the clonally amplified target polynucleotides are derived from a single polynucleotide molecule; and
b) sequencing the amplification products of a) in a plurality of microcapsules.

15. The method according to claim 14, further comprising:
c) analyzing the sequencing products of b) in a capillary electrophoresis system.

16. The method according to claim 15, wherein said microcapsules are inserted into the capillaries of said system and said sequencing products are released from said microcapsules into said capillaries.

17. The method according to claim 14, wherein at least one of said microcapsules comprises a hydrogel.

18. The method according to claim 14, wherein at least one of said microcapsules is a colloidosome.

19. The method according to claim 14, wherein at least one of said microcapsules is produced by layer-by-layer polymer deposition.

20. The method according to claim 14, wherein at least one of said microcapsules is produced by polymer deposition.

21. The method according to claim 14, wherein said sequencing is Sanger sequencing.

22. The method according to claim 14, wherein said sequencing is pyrosequencing.

* * * * *